(12) United States Patent
Kanner

(10) Patent No.: US 8,038,939 B2
(45) Date of Patent: Oct. 18, 2011

(54) METHOD AND DEVICES FOR IMPROVED DISINFECTION PROCESS

(75) Inventor: Rowland W. Kanner, Guntersville, AL (US)

(73) Assignee: Atrion Medical Products, Inc., Arab, AL (US)

(*) Notice: Subject to any disclaimer, the term of this patent is extended or adjusted under 35 U.S.C. 154(b) by 0 days.

(21) Appl. No.: 12/627,736

(22) Filed: Nov. 30, 2009

(65) Prior Publication Data

US 2010/0310429 A1    Dec. 9, 2010

Related U.S. Application Data

(60) Provisional application No. 61/185,277, filed on Jun. 9, 2009.

(51) Int. Cl.
*A61L 2/00* (2006.01)
*A61L 2/20* (2006.01)
*A61L 2/18* (2006.01)
*C12M 1/00* (2006.01)

(52) U.S. Cl. ............... 422/28; 422/29; 422/30; 422/34; 422/35; 422/36; 422/37; 435/283.1

(58) Field of Classification Search .............. 422/28, 422/29, 30, 34, 35, 36, 37; 435/283.1
See application file for complete search history.

(56) References Cited

U.S. PATENT DOCUMENTS

| | | | |
|---|---|---|---|
| 3,770,113 A | 11/1973 | Thomas | |
| 4,013,410 A | 3/1977 | Thomas et al. | |
| 4,200,187 A | 4/1980 | Thomas | |
| 4,637,919 A | 1/1987 | Ryder et al. | |
| 4,750,610 A * | 6/1988 | Ryder | 206/5.1 |
| 4,807,750 A | 2/1989 | Ryder et al. | |
| 4,817,998 A | 4/1989 | Ryder et al. | |
| 4,824,557 A | 4/1989 | Cartmell et al. | |
| 4,889,693 A | 12/1989 | Su et al. | |
| 4,890,729 A | 1/1990 | Ranalletta | |
| 4,940,542 A | 7/1990 | Simizu et al. | |
| 4,956,156 A * | 9/1990 | Kanner et al. | 422/300 |
| 4,981,657 A | 1/1991 | Ryder | |
| 4,996,027 A * | 2/1991 | Kanner | 422/113 |
| 5,059,402 A | 10/1991 | Seamons et al. | |
| 5,196,174 A | 3/1993 | Cerola et al. | |
| 5,250,266 A * | 10/1993 | Kanner | 422/113 |
| 5,270,002 A * | 12/1993 | Neff et al. | 422/30 |
| 5,292,488 A | 3/1994 | Cerola et al. | |
| 5,306,352 A | 4/1994 | Nicolson et al. | |
| 5,366,078 A * | 11/1994 | Braun | 206/5.1 |
| 5,468,448 A | 11/1995 | Nicolson et al. | |
| 5,558,846 A * | 9/1996 | Alvord et al. | 422/301 |
| 5,609,837 A * | 3/1997 | Cerny et al. | 422/301 |
| 5,690,211 A | 11/1997 | Jao et al. | |
| 5,958,351 A | 9/1999 | Cerny et al. | |
| 5,972,292 A * | 10/1999 | DeMeo | 422/25 |
| 2001/0017271 A1 | 8/2001 | Yavitz | |
| 2005/0081928 A1 | 4/2005 | Burke et al. | |

(Continued)

*Primary Examiner* — Robert Warden
(74) *Attorney, Agent, or Firm* — Clark Hill PLC

(57) ABSTRACT

A method which enhances a disinfection process by using a catalyst which increases in effective surface area during the process. Also disclosed are contact lens disinfecting systems which are designed to maintain a high concentration of hydrogen peroxide solution for a longer period of time before increasing the overall surface area of catalyst exposed to the hydrogen peroxide solution. The devices utilize pressure from expanding oxygen generated within the system through use of a small catalyst, or through exposure of only a small portion of a large catalyst, to control deployment of the large catalyst for completing disproportionation of the hydrogen peroxide.

26 Claims, 17 Drawing Sheets

U.S. PATENT DOCUMENTS

2005/0087453 A1    4/2005   Mahieu et al.
2005/0263412 A1    12/2005   Huang
2008/0134577 A1    6/2008   DeVries
2008/0185298 A1    8/2008   Kanner et al.

* cited by examiner

METHOD AND DEVICES FOR IMPROVED DISINFECTION PROCESS

RELATED APPLICATION (PRIORITY CLAIM)

This application claims the benefit of U.S. Provisional Application Ser. No. 61/185,277, filed Jun. 9, 2009, which is hereby incorporated herein by reference in its entirety.

BACKGROUND

The present invention generally relates to methods and apparatus for controlling the decomposition of a solution using a catalyzing agent, and more specifically relates to a method and apparatus for controlling and enhancing a disinfection process.

The present invention relates to an improved disinfection method and apparatus which utilizes, for example, hydrogen peroxide solution and a catalyzing agent to facilitate controlled decomposition of the hydrogen peroxide within a sealed reaction chamber containing an object to be disinfected, such as contact lenses, wherein the solution, the decomposition catalyzing agent, the resulting energy, and byproducts of decomposition are employed to control and enhance the disinfection process.

While the method disclosed herein may be utilized, for example, to disinfect contact lenses, particularly soft contact lenses, the method may also be suitable to disinfect other types of items, for example larger items, such as non-sterile medical or dental appliances and the like, within a reaction chamber appropriately scaled to size. As such, while the present disclosure focuses on using the method (and associated apparatus) to disinfect contact lenses using hydrogen peroxide, it should be understood that the method can be used in other disinfecting applications.

Hydrogen peroxide is unstable and eventually decomposes (disproportionates) into water and oxygen over time. The decomposition occurs more quickly if the hydrogen peroxide is, for example, subjected to temperature extremes, exposed to ultraviolet light, or introduced to a catalyzing agent. The decomposition rate is also affected by its percentage of concentration, its pH, and the presence of impurities and stabilizers. The decomposition process is exothermic in nature and when a catalyzing agent has been introduced to the hydrogen peroxide, evolved thermal energy and oxygen can accelerate the process by several means that increase molecular contact opportunities with the catalyzing agent. The means include creation of thermally inspired convection, mechanical mixing resulting from the stirring effect of rising oxygen bubbles, as well as increased molecular motion which lowers the energy threshold for decomposition.

Hydrogen peroxide is a larger molecule than water with a specific gravity of 1.443 and a viscosity of 1.245 cP at 20 degrees Celsius, compared to water which has a viscosity of 1.003 cP at 20 degrees Celsius. Nevertheless, each is entirely miscible with the other, allowing a limitless variety of concentration levels to be tailored to suit various applications. Hydrogen peroxide solutions formulated for disinfection may contain surfactants, and are often pH-modified and chemically-stabilized in order to assure reasonable shelf life and potency at the time of use. Hydrogen peroxide formulated for disinfection of contact lenses, for example, is generally supplied at a concentration of no less than 3.0%, and may range up to 4.0% in order to assure that a minimum concentration of 3.0% is available for disinfection.

While more highly concentrated solutions would be more potent and effective against pathogens, the use of more highly concentrated solutions has generally not been pursued for contact lens care use. This is due to the strong oxidizing nature of hydrogen peroxide, and the damaging effects such higher concentrations could have upon accidental, full strength contact with sensitive ocular tissue. Typically, peroxide for the purpose of disinfecting contact lenses is supplied at 3.7% concentration.

Catalysts that facilitate decomposition of hydrogen peroxide include most of the transition metals, manganese dioxide, silver and the enzyme catalase. Quite commonly in connection with single step contact lens disinfection systems, platinum is introduced to the solution in the form of a surface coating on a polymeric support structure. Catalysts function by changing the energy pathway for a chemical reaction. FIG. 1 provides a graph which compares the energy associated with activating without a catalyst (line 10) to the energy associated with activating with a catalyst (line 12). As indicated, when introduced to hydrogen peroxide, a catalyst serves to lower the activation energy required to initiate decomposition of the hydrogen peroxide under ambient conditions in which it was otherwise stable.

The combination of solution temperature, exothermally-generated heat, thermally-inspired convection, mechanical stirring from evolving oxygen bubbles, dilution resulting from disproportionation, dissolved gas in the solution, and changes in ambient pressure has been found to impact the rate at which the catalyzed reaction progresses. In an open environment such as that provided by a typical commercially-available hydrogen peroxide disinfection cup system for contact lenses, for example the AO SEPT system (as shown in FIG. 2, with the overall system being identified with reference numeral 13) offered by Ciba Vision, contact lenses are introduced to 10 milliliters of the hydrogen peroxide solution essentially simultaneously with the catalyst, and evolved oxygen from the reaction is subsequently vented off through a hydrophobic membrane or one way valve (indicated with reference numeral 14 in FIG. 2) in the cap (indicated with reference numeral 15 in FIG. 2). As shown in FIG. 3, with this type of system, solution concentration resulting from the catalyzed reaction declines rather rapidly to about 0.1%, whereupon six to eight hours are required before the concentration of the solution bath has been reduced to a level that is safe for a disinfected lens to be inserted in the eye without risk of ocular irritation to the user.

Disinfection of contact lenses is regularly practiced by lens wearers in order to eliminate a variety of environmentally ubiquitous organisms known to be found on contaminated lenses. The organisms at issue include, but are not limited to, various pathogenic strains of *Staphylococcus, Pseudomonas, E. Coli, Acanthamoeba*, and the like. *Acanthamoeba* is an opportunistic pathogen associated with a potentially blinding infection of the cornea termed *Acanthamoeba keratitis*. Among the general population, contact lens wearers are believed to be most at risk to this organism, accounting for more than 95% of reported cases of the ocular infection. A particularly insidious organism, *Acanthamoeba* can transition from active trophozoite to a dormant, more resistant encysted stage when exposed to conditions of starvation, desiccation, and changes in pH and temperature. Once encysted, this organism's resistance to biocides results largely from the physical barrier of its cyst walls rather than as a consequence of metabolic dormancy. The major components of the cyst's walls are acid-resistant proteins and cellulose, with the outer wall, or exocyst, composed primarily of protein and the inner endocyst comprised of over 30% cellulose. Although remarkably resistant to chlorine-hearing disinfectants and even hydrochloric acid, encysted *Acan-* thamoeba is subject to destruction by exposure to hydrogen peroxide. *Acanthamoeba* cysts exhibit greater susceptibility to hydrogen peroxide as the disinfectant's concentration is increased. The impact of hydrogen peroxide's concentration upon *Acanthamoeba* cysts was documented in a study by Reanne Hughes, Peter W. Andrew and Simon Kilvington of the Department of Microbiology and Immunology, University of Leicester, Leicester, UK, published in the May 2003 edition of *"Applied and Environmental Microbiology"*. A graph extracted from that study and shown in FIG. 4 illustrates the impact of 1%, 2% and 3% hydrogen peroxide solutions over a period of time upon killing the target *Acanthamoeba* cyst. In FIG. 4, line 20 relates to the 1% hydrogen peroxide solution, line 22 relates to the 2% hydrogen peroxide solution, and line 24 relates to the 3% hydrogen peroxide solution.

Under standard ambient conditions, the method by which hydrogen peroxide destroys pathogens is through oxidation resulting in denaturation of the organism's proteins. One option to deal with heavily contaminated lenses or resistant organisms, such as *Acanthamoeba*, would be to start with a more highly concentrated solution, but there are undesirable user risks associated with that approach. Some of these risks have already been discussed hereinabove.

A more attractive option would be to slow the decomposition process in order to maintain a higher concentration of hydrogen peroxide for a longer period of time before finally reducing the concentration to an ocularly comfortable level. With such an approach, more heavily contaminated lenses could therefore be disinfected, and resistant organisms could be better dealt with using solutions that have commonly-accepted concentrations. Unfortunately, present day disinfection systems are limited by the reaction rate necessary to obtain irritation-free disinfected lenses at the end of a reasonable 6 to 8 hour overnight wait period. This results from a balance that has historically been struck between the volume of peroxide solution, a safe and practical starting concentration level for the peroxide, and the size of catalyst (such as platinum) necessary to assure adequate decomposition in use. Regarding catalyst size, typically 94 square millimeters to 141 square millimeters of catalyst surface area is allocated for each milliliter of 3.0% to 4.0% hydrogen peroxide solution. Although an undersized catalyst would certainly slow the decomposition process, keeping concentrations higher for a longer period of time, using an undersized catalyst may result in the lens solution not reaching user comfort levels within a reasonable time period, since the significance of catalyst surface area actually increases as the amount of released energy and solution concentration declines. Additionally, methods (such as is disclosed in U.S. Pat. No. 5,468,448) of slowing decomposition by using buoyant catalysts that have contact areas which increase as they sink from loss of attached bubbles have proven too difficult to commercialize reliably.

OBJECTS AND SUMMARY

An object of an embodiment of the present invention is to provide an improved disinfection method.

Another object of an embodiment of the present invention is to provide an apparatus which can be used to practice the method.

Briefly, a specific embodiment of the present invention provides a method which can be used to disinfect, for example, contact lenses using hydrogen peroxide and a catalyst. The method provides that once the catalyst is introduced to the hydrogen peroxide in a reaction chamber, such as in a contact lens case, and the reaction chamber is sealed, the overall surface area of catalyst exposed to the hydrogen peroxide increases during the process, thereby allowing improved disinfection while providing means to assure satisfactory decomposition of the hydrogen peroxide solution within a reasonable time period.

BRIEF DESCRIPTION OF THE DRAWINGS

The organization and manner of the structure and operation of the invention, together with further objects and advantages thereof, may best be understood by reference to the following description, taken in connection with the accompanying drawing, wherein.

DESCRIPTION

Figure 1:
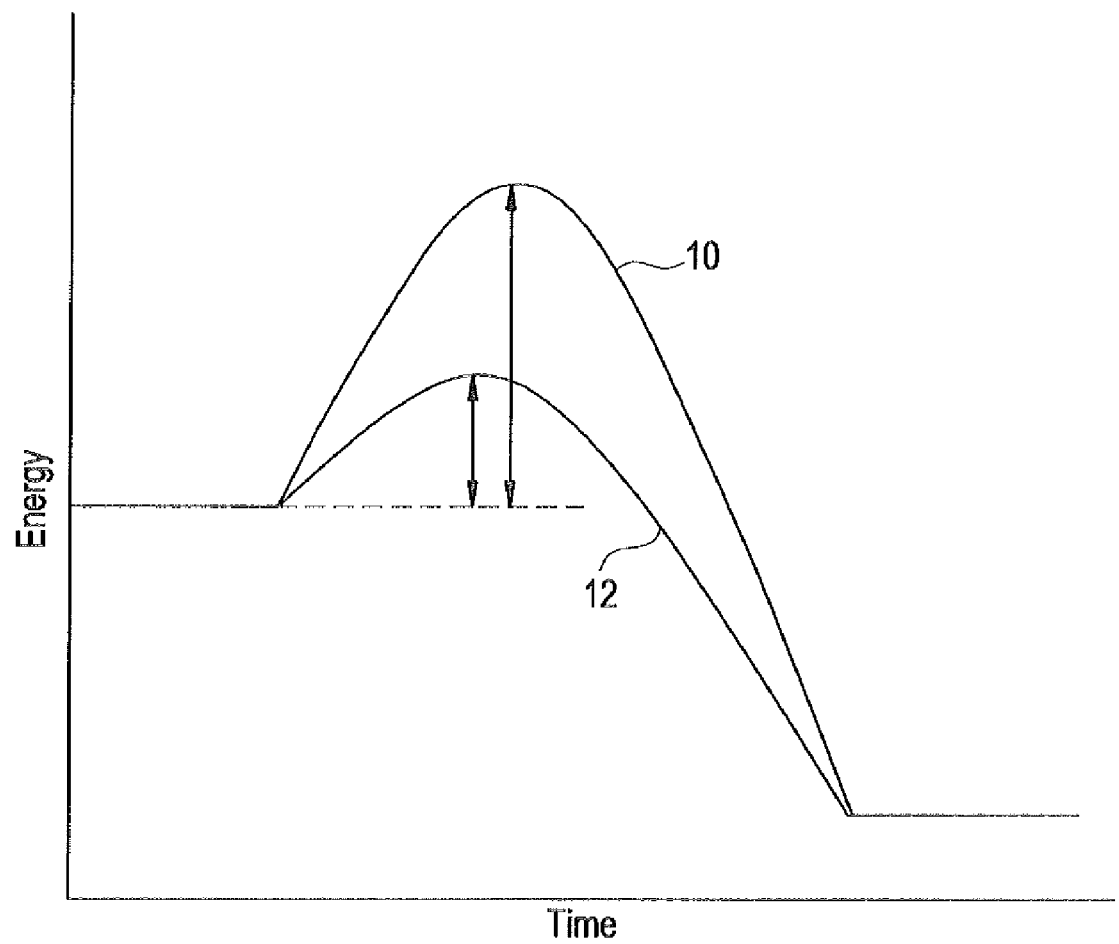
FIG. 1 is a graph which effectively compares the energy associated with activating without a catalyst to the energy associated with activating with a catalyst.

The inventions disclosed herein are susceptible to embodiment in many different forms. However, specific embodiments are shown in the drawings and described in detail hereinbelow. The present disclosure is to be considered an example of the principles of the invention, and is not intended to limit the invention to the specific embodiments which are illustrated and described herein.

Figure 2:
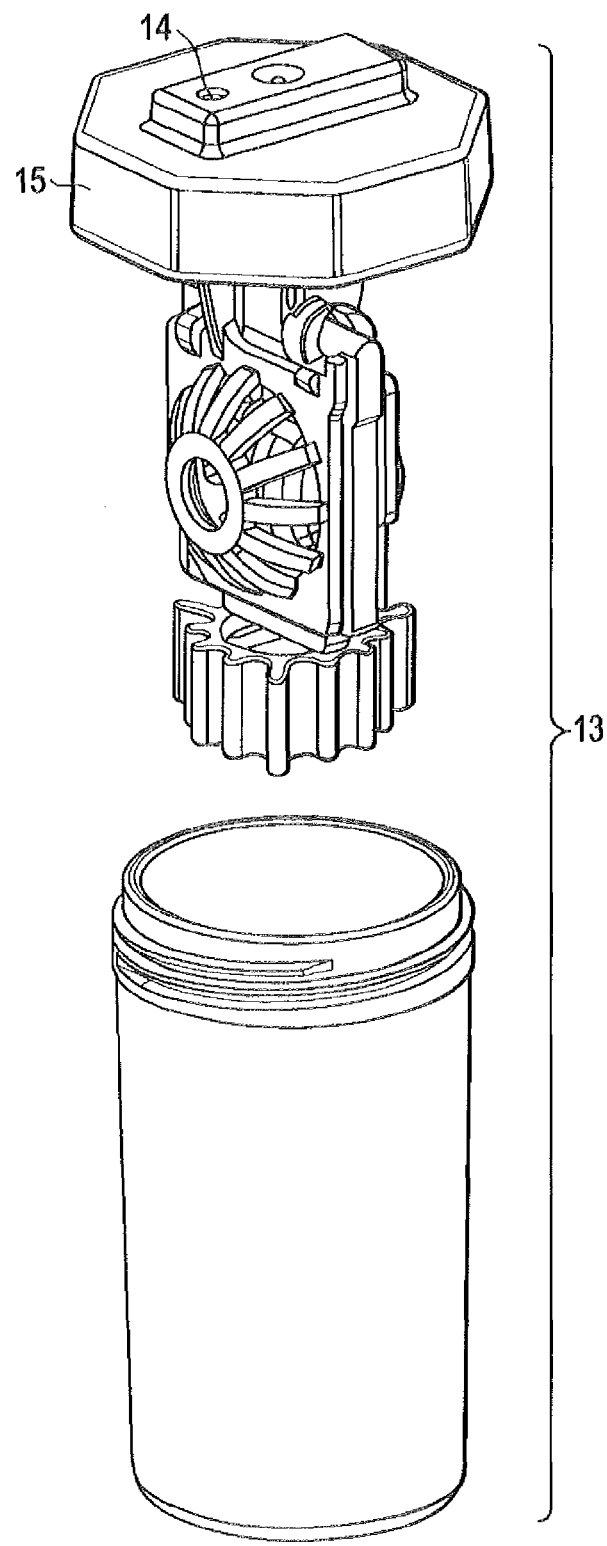
FIG. 2 is a perspective view of a prior art contact lens disinfection cup system, specifically the AO SEPT system offered by Ciba Vision.

The method disclosed herein improves the disinfection process by harnessing energy from the decomposition process. Useful energy is available during the catalytically-inspired disproportionation of hydrogen peroxide solution in the form of heat and expansion of evolved oxygen molecules. Containment of the liberated oxygen from 10 milliliters of solution within a reaction chamber having 4 cc of head space, a volume similar to the typical contact lens cup discussed above (and illustrated in FIG. 2), has the potential to generate approximately 186 p.s.i. pressure within one half hour following introduction of a catalyst having 948 square millimeters of surface area. Although a catalyst having more than 94 to 141 square millimeters of surface area for each milliliter of solution would serve to decrease hydrogen peroxide solution concentration too quickly for effective disinfection in a typical disinfection system, introducing such a catalyst on a delayed basis has been found to offer improved disinfection possibilities not otherwise available.

A metallic catalyst introduced to a dilute hydrogen peroxide solution must contact the hydrogen peroxide molecules in order to initiate their decomposition into water and oxygen. Adjacent molecules of the water diluent, evolved oxygen and the newly-formed water will only serve to insulate other peroxide molecules from contacting the catalyst. It can therefore be seen that movement of the solution to displace water and oxygen and bring more peroxide molecules into contact with the catalyst will accelerate the rate of decomposition over a static condition. The higher surface area: fluid volume ratio of a larger catalyst is therefore more effective in bringing end reaction concentrations to lower, ocularly safe levels within a shorter amount of time as bubbles of oxygen resulting from catalytic decomposition of the peroxide solution rise to the surface and provide mechanical mixing of the peroxide solution in combination with convection currents inspired by the reaction evolved heat.

Upon being introduced to peroxide solution of the same concentration, larger catalysts therefore provide higher initial rates of activity per unit of catalyst surface area than smaller catalysts due to their generation of more heat and evolved oxygen per unit of peroxide solution volume. In contrast, small catalysts offering very low surface area: fluid volume ratios cannot create the necessary mixing from evolved oxygen and heat to promote sufficient flow within the peroxide solution body to overcome a tendency for the solution to stratify. Elevated hydrostatic pressure resulting from containment of evolving oxygen also increases the amount of dissolved oxygen that can be absorbed within the solution. High hydrostatic pressure combined with oxygen entering into solution can also slow the reaction by raising the level of activation energy required for decomposition (see FIG. 1). Viewed strictly from a mechanical perspective, although diffusion ultimately will balance the concentration of solution throughout the fluid body over time, hydrogen peroxide has been found to be subject to short term stratification when decomposition initiated by a small catalytic structure generates only minimal heat and oxygen bubbles and those oxygen molecules not entering into solution under pressure form bubbles of much smaller size leading to decreased mechanical mixing of the solution bath as they rise to the surface.

Another object of the method disclosed herein is to enhance the disinfection process by obtaining an additive effect from the energy and byproducts of the decomposition phase. By employing high pressure from contained, expanding, evolved oxygen in order to assist a hydrogen peroxide solution in obtaining greater penetration and oxidative potential, the high hydrostatic conditions thereby created can also be leveraged to exploit the natural dynamic equilibrium of pathogens, as diffusion allows for an elevated oxygen condition to be created within the organism under oxygen-saturated conditions sustained by the pressurized solution bath. A further additive effect can thereafter be realized as a consequence of introducing a subsequent rapid decompression from the high pressure condition to elicit boiling of dissolved oxygen from solution and thereby cause expansion of excess absorbed oxygen within the pathogen to further stress the organism's cell membrane undergoing oxidative denaturation from hydrogen peroxide exposure. This mechanism compliments the destructive effects of oxidative denaturation upon the pathogen's proteins. Following decompression, with high pressure having been relieved, the catalytic reaction is therefore allowed to resume under low pressure at a much faster pace in order to assure that decomposition has been completed to an acceptable level within the desired 6 to 8 hour time span.

It is important to discriminate between the true overall surface area of a catalyst utilized within this application and the effective surface area of that catalyst. Experience has shown for instance, that when horizontal and downward facing surfaces of the catalyst are placed in close proximity to an opposing surface, that location on the catalyst exhibits a very low decomposition activity level for the amount of surface area exposed to the peroxide solution. This apparent lack of effectiveness is due to inhibited free solution flow resulting from the narrow horizontal space confronting the catalyst and an accumulation of attached oxygen bubbles from decomposed peroxide adhering to these adjacent surfaces and remaining trapped within the narrow horizontal space. Oxygen bubbles trapped in this manner cannot rise away from the catalyst and therefore remain attached to its surface, reducing the amount of catalytic surface area exposed to the hydrogen peroxide and thus impose a very significant decrease upon the rate of peroxide decomposition for that surface of the catalyst. Further, the close proximity of the adjacent surfaces, the trapped bubbles and the resulting narrow passageways created by these conditions inhibit free out flow of evolved water from the decomposition process and therefore the inflow of fresh hydrogen peroxide to be broken down. Exposed vertical catalytic surfaces provide for the highest rate of hydrogen peroxide decomposition because the evolved oxygen bubbles are immediately buoyed upward, away from the catalyst along with evolved water that has been warmed by heat from the reaction. Convection inspired flow resulting from these energy sources tends to stir the solution, helps carry off the water and introduces fresh hydrogen peroxide to the catalyst's surfaces. It can therefore be seen that as long as the catalyst's vertical surfaces are freely exposed to the peroxide solution they are effective in accelerating its decomposition by inspiring a continuous flow of fresh peroxide against the catalysts surfaces. If a catalyst's vertical surfaces are obstructed by close adjacent surfaces and therefore not freely exposed however, they will quickly become ineffective as evolved oxygen bubbles become trapped between the adjacent surfaces. When this happens, the catalyst's activity level quickly decreases in a cascade of events very much like those previously discussed for close fitting adjacent horizontal surfaces. As a result, it has been clearly shown that closely-spaced adjacent vertical surfaces from opposing structures can significantly decrease the activity of the vertically disposed catalytic surfaces due to oxygen bubble attachment, decreased evolved energy and inhibited fluid exchange. This mechanism can therefore be utilized to control the effective surface area offered by a catalyst without any need whatsoever to actually prevent physical contact between hydrogen peroxide and the catalyst's surfaces. By this method, a large catalyst can also be made to perform like a catalyst of much smaller size until the close fitting adjacent structure is removed.

Figure 3:
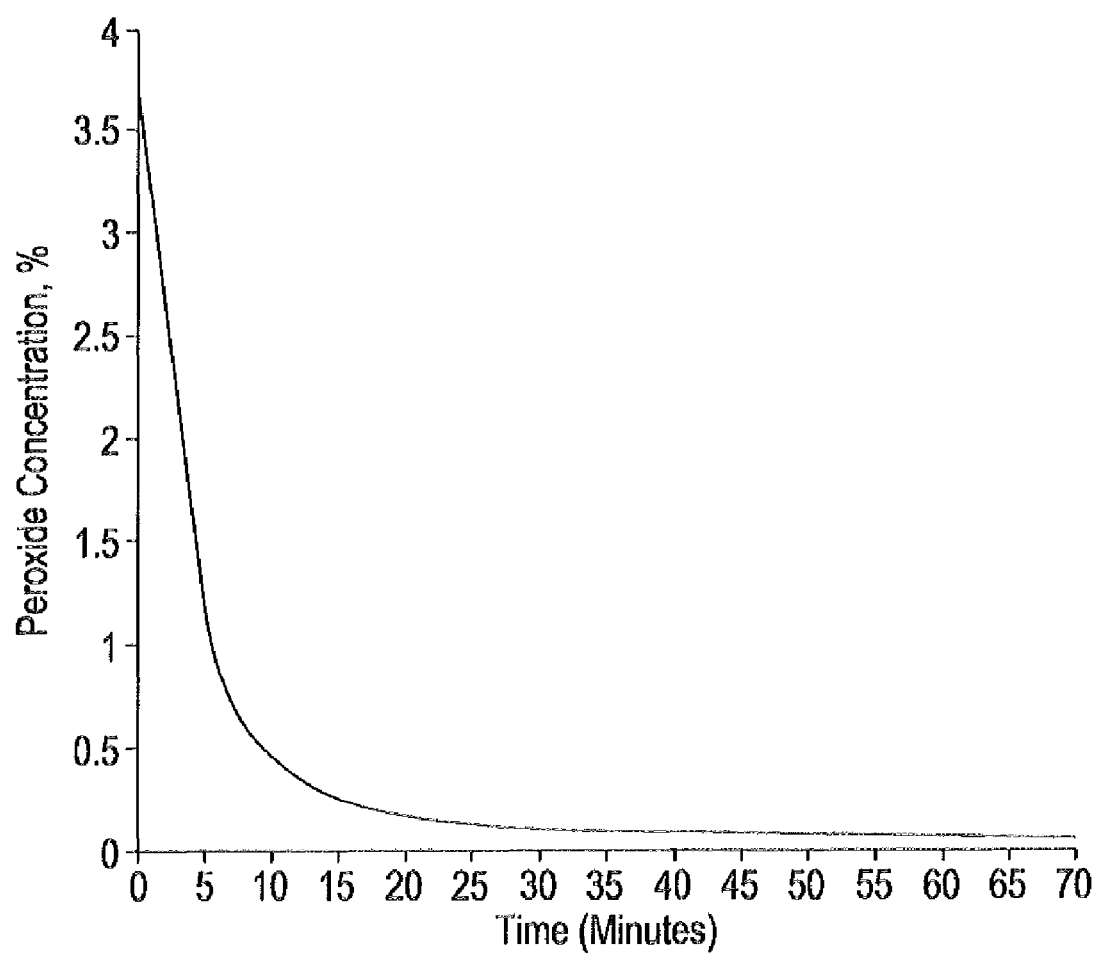
FIG. 3 is a graph which indicates the change in concentration of a hydrogen peroxide solution over time, when the cup system shown in FIG. 2 is used to disinfect contact lenses.
Figure 6:
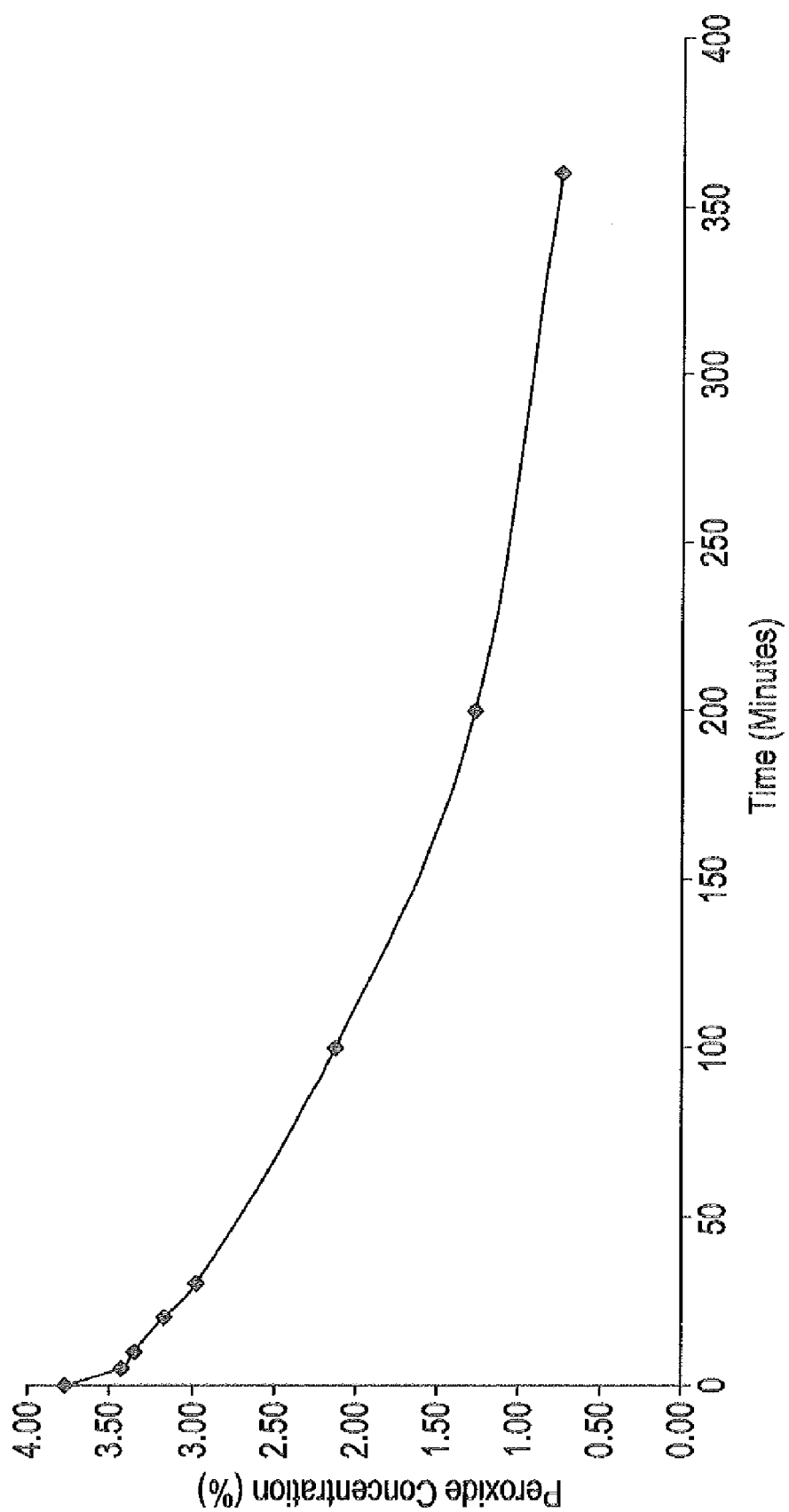
FIG. 6 is similar to FIG. 5, but shows the change in peroxide concentration over time when a 110 sq. mm catalyst is immersed in 10 milliliters of 3.7% hydrogen peroxide solution.
Figure 7:
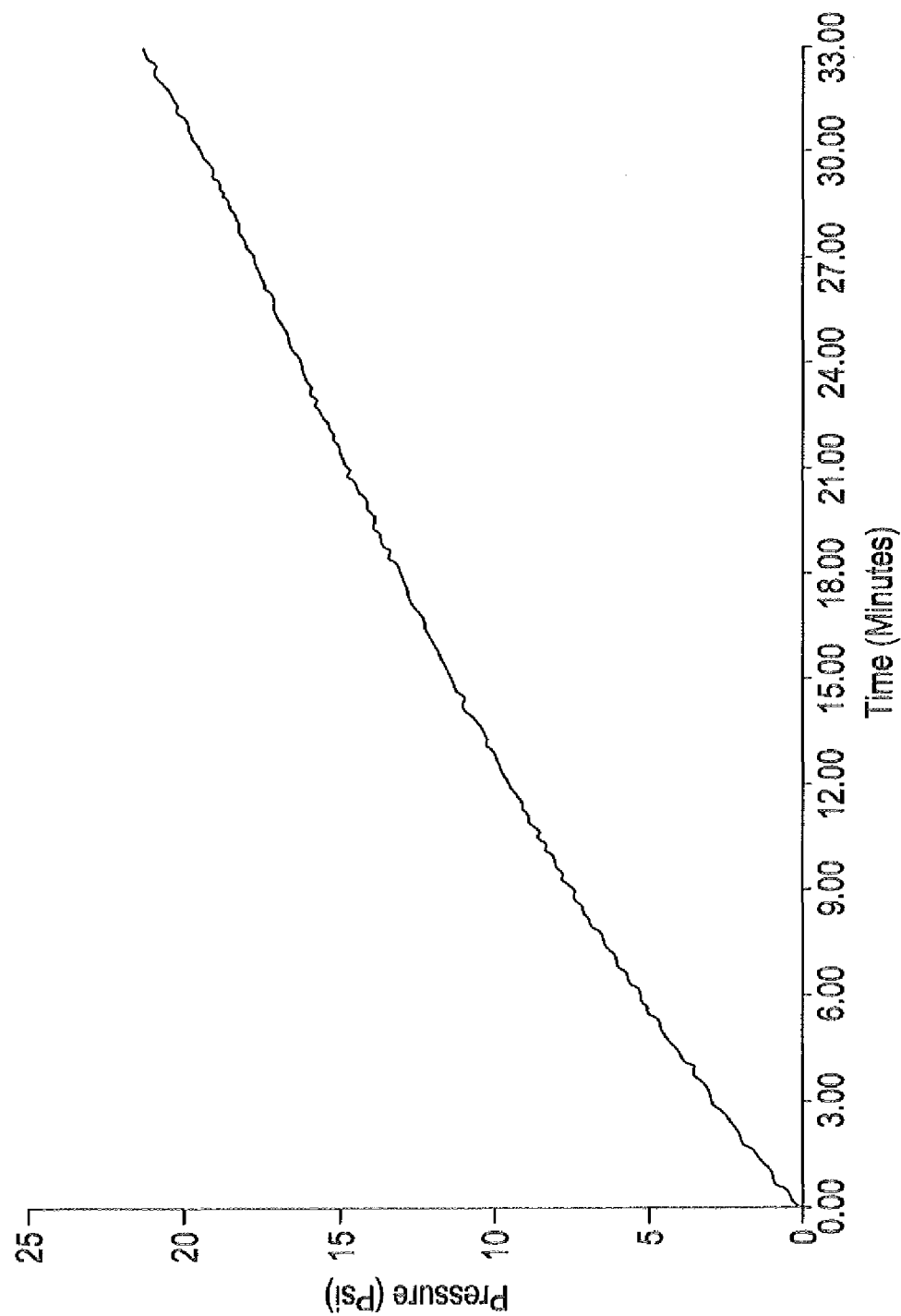
FIG. 7 is a graph which shows the change in pressure over time when a 67 sq. mm catalyst is immersed in 10 milliliters of 3.7% hydrogen peroxide solution in a container having 8 cc's of headspace.

Regardless of active surface area, whether large or small, each catalyst will create pressure within a closed system as oxygen is evolved. Under identical ambient conditions, the rate at which this pressure is generated depends upon both the catalyst's effective surface area and the concentration of the peroxide it has been introduced into. Immersing a smaller catalyst, one having 110 sq. mm of effective surface area in 10 milliliters of 3.7% hydrogen peroxide solution for example, will generate 59 p.s.i. of pressure within 30 minutes in a container having 6 cc's of headspace and approximately 100 p.s.i. after 60 minutes (see FIG. 5) and 150 p.s.i. in 120 minutes when headspace is limited to 4 cc's of volume. With this small catalyst, solution concentration will reduce to 3.0% after 30 minutes immersion and 2.6% after 60 minutes from the starting concentration of 3.7% (see FIG. 6), compared against a miniscule 0.1% concentration (see FIG. 3) resulting from 30 minutes immersion of a standard sized catalyst of 940 sq. mm surface area. Immersing an even smaller catalyst, one having 67 sq. mm of effective surface area in 10 milliliters of solution having 8 cc's of headspace results in 19 p.s.i. pressure and 3.3% solution concentration after 30 minutes (see FIG. 7).

Figure 4:
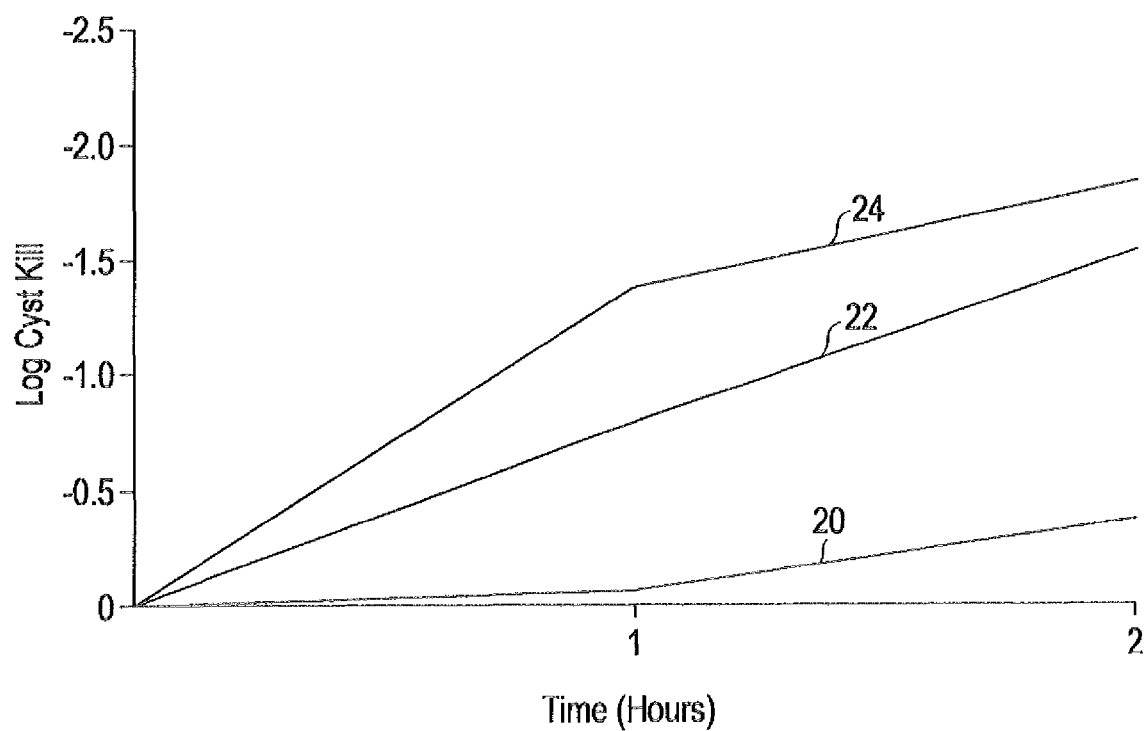
FIG. 4 is a graph which shows the impact of 1%, 2% and 3% hydrogen peroxide solutions over a period of time upon killing the target *Acanthamoeba* cyst.
Figure 8:
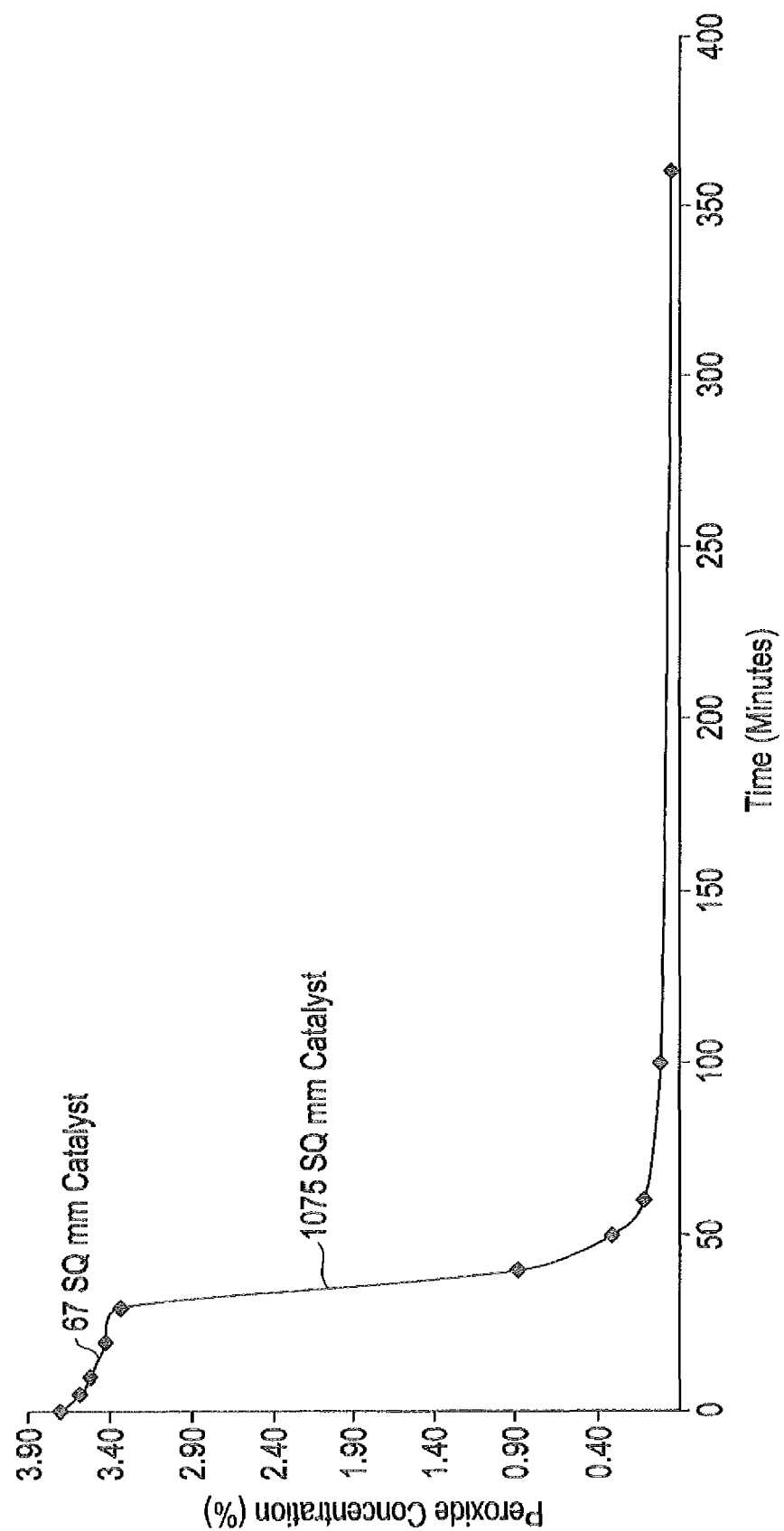
FIG. 8 is a graph which shows the change in peroxide concentration over time when a 67 sq. mm catalyst is first subjected to 10 milliliters of 3.7% hydrogen peroxide solution in a standard cup having 8 cc's of headspace, and then followed by a 1075 sq. mm catalyst after 30 minutes from start.
Figure 9:
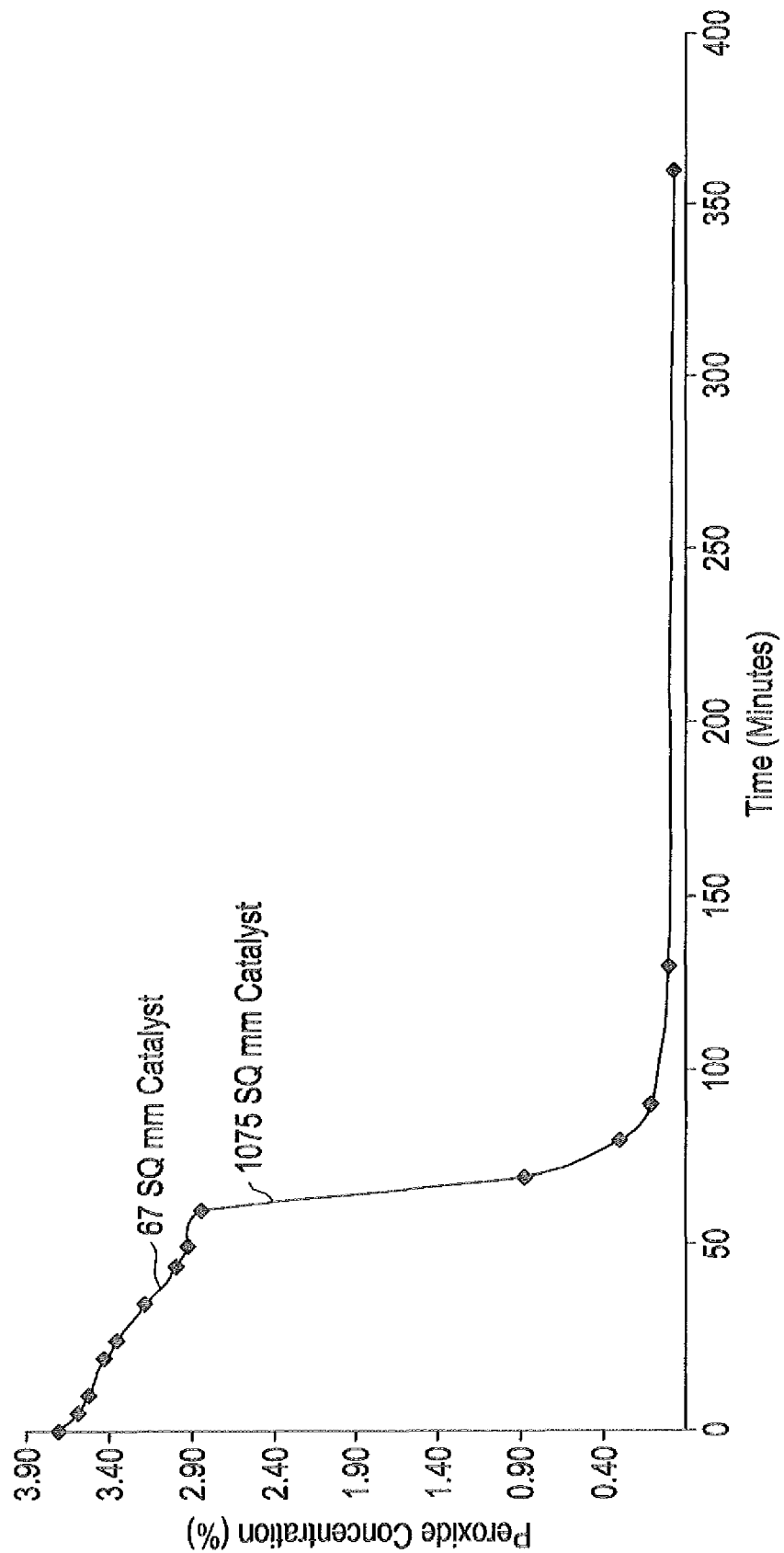
FIG. 9 is similar to FIG. 8, but shows the change in peroxide concentration over time when the secondary 1075 sq. mm catalyst is introduced 60 minutes from start, as opposed to 30 minutes from start.

It can therefore be seen that utilization of a low activity level catalyst having, for instance, 65 to 110 sq. mm effective surface area, provides pressure to do work and offers the benefit of sustaining a higher hydrogen peroxide concentration for a longer period of time. One can also see that such a delay offers several orders of magnitude improvement in the ability to kill *Acanthamoeba* organism cysts in greater quantity. Referring to FIG. 4, the log cyst kill for a 3% peroxide concentration (represented by line 24) held for 30 minutes is −0.75 and for 60 minutes is −1.40 compared to only −0.067 for even a 1% solution (represented by line 20) held for a 60 minute period. Unfortunately, a catalyst of 65 to 110 sq. mm does not have the ability to decompose 10 milliliters of hydrogen peroxide to ocularly save levels within the desired 6 to 8 hour time span. Therefore, following the delay period offered by this small catalyst it has been shown necessary to introduce a catalyst of much greater surface area, one capable of providing peroxide decomposition at a substantially higher rate, in order to reduce peroxide concentrations to the desired level within time remaining after the desirable 30 or 60 minute delay. Ideally, this larger secondary catalyst should offer a minimum of 960 sq. mm of additional surface area but would fit within a present day cylindrical lens disinfection case if made as large as 1777 sq. mm in active surface area in order to complete decomposition within 6 to 8 hours from introduction of the catalyst assembly and lenses. The peroxide decomposition curve in FIG. 8 shows the decline of concentration for a 10 milliliter body of 3.7% solution first subjected to a 67 sq. mm catalyst, then followed by a 1075 sq. mm catalyst after 30 minutes from start. FIG. 9 illustrates the desirable concentration curve possible when using an initial 67 sq. mm effective area catalyst followed with a secondary 1075 sq. mm catalyst after 60 minutes from start. FIG. 9 does not illustrate the maximum time delay possible, however. Provided that a secondary catalyst of large enough area were presented, one of 1777 sq. mm of active surface area for example following initial decomposition with a small active surface area catalyst, delays of more than 60 minutes are possible when using larger catalysts than the 1075 sq. mm catalyst in the curves shown in FIGS. 8 and 9.

FIGS. 10-13 illustrate two contact lens disinfection systems 100, 200 which are in accordance with embodiments of the present invention. The systems 100, 200 shown in FIGS. 10-13 are designed to maintain a high concentration of peroxide for a longer period of time before introducing a larger catalyst than commonly used in a typical single step hydrogen peroxide disinfection system. Both devices utilize pressure from expanding oxygen generated within the system through use of a small catalyst, or through exposure of only a small portion of a large catalyst, to control deployment of the large catalyst for completing disproportionation of the peroxide. The catalyst assembly can therefore be comprised of a pair of catalytic members offering a low catalytically active surface area initially, followed by deployment of one of the members to expose a much greater catalytic surface area to the peroxide disinfection solution. In other words, the catalyst assembly is basically expandable with regard to overall surface area. Experience has shown that the effective activity level of a catalyst's horizontal surfaces are less than that of its vertical surfaces and that a downward facing horizontal surface offers the least effective catalytic activity of these three orientations, especially when placed in close proximity to the bottom of the containment vessel. It has also been experienced that the effectiveness of even vertical catalyst surfaces, when placed in very close proximity to adjacent structures, is significantly inhibited due to the inability of these surfaces to encounter fresh hydrogen peroxide and also as a result of generated oxygen bubbles that cling between these close surfaces. The devices shown in FIGS. 10-13 also feature a pneumatic pressure control mechanism in the form of a pressure sensitive, one way, low pressure control valve that both sustains low pressure venting and prevents entry at all times of undesirable organisms or particles into the disinfection system.

The contact lens disinfection system 100 illustrated in FIGS. 10 and 11 will be described initially, and then the contact lens disinfection system 200 illustrated in FIGS. 12 and 13 will be described, mainly discussing the differences between the two systems.

Figure 10:
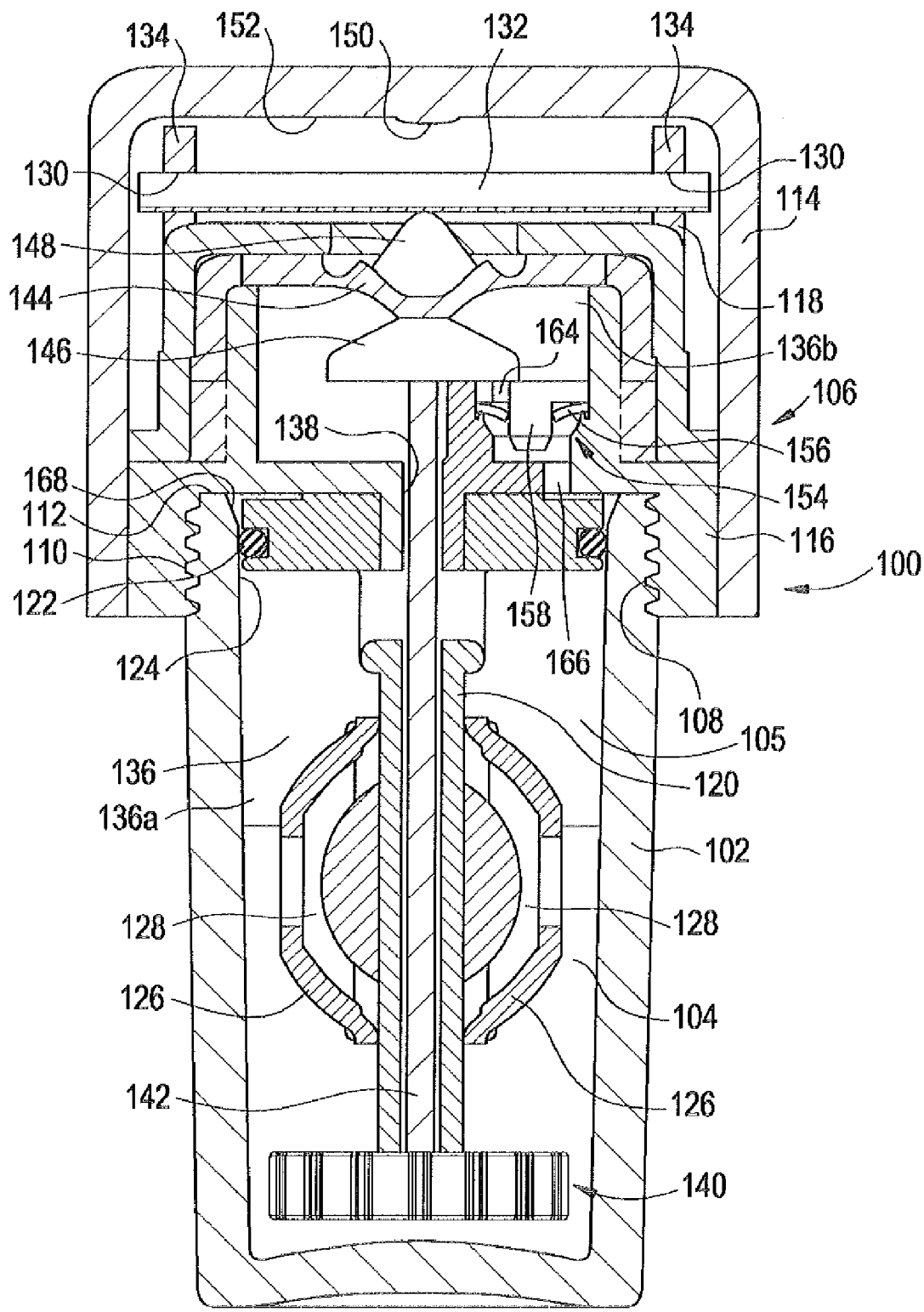
FIGS. 10 and 11 are cross-sectional views of a contact lens disinfecting system which is in accordance with an embodiment of the present invention.
Figure 11:
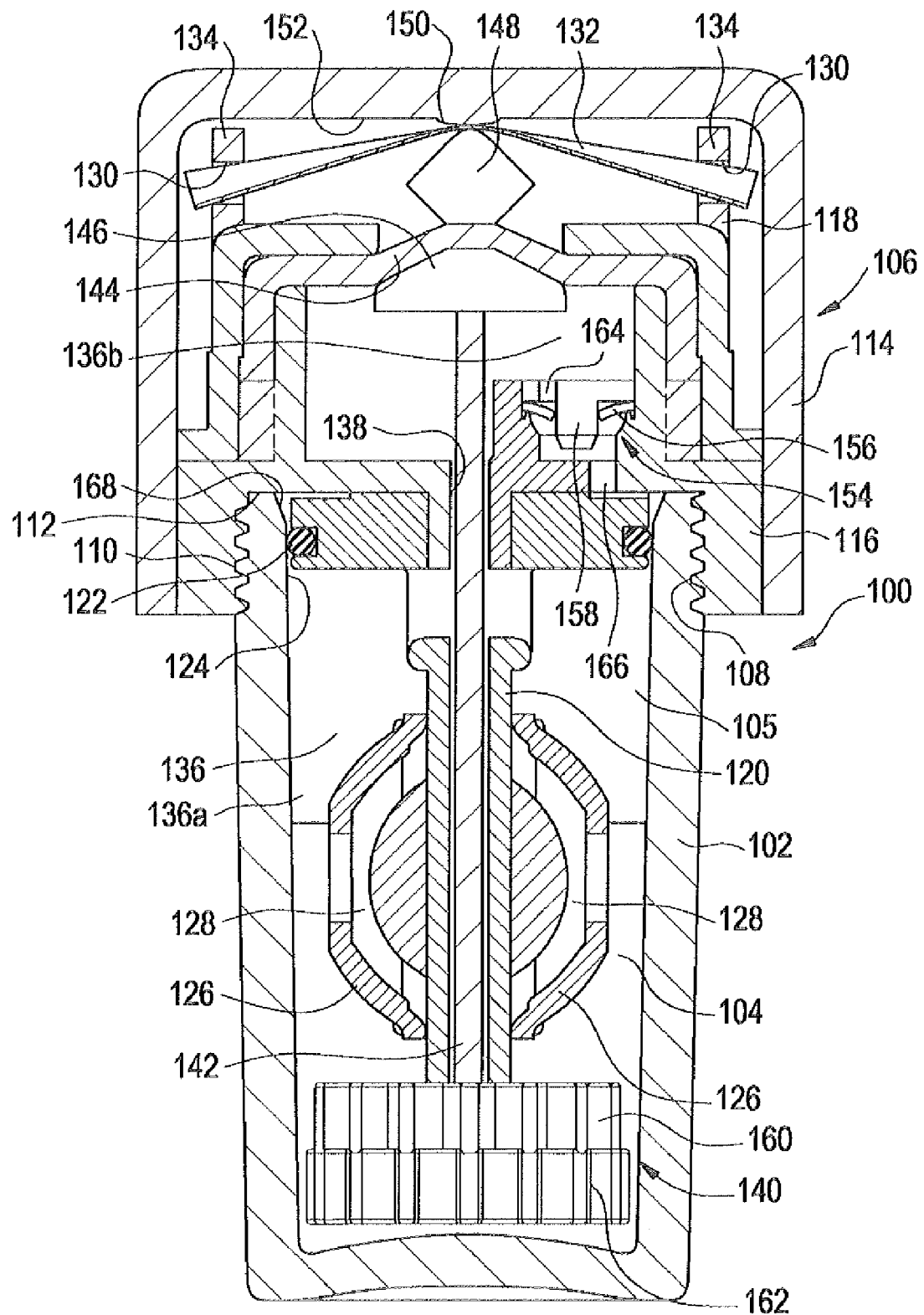

The contact lens disinfection system 100 illustrated in FIGS. 10 and 11 includes a cup 102 for holding hydrogen peroxide solution 104 (typically 10 milliliters of solution), and the cup 102 is conventional in that it is generally cylindrical and provides a reaction chamber 105 therein for disinfecting contact lenses. The system 100 includes a cap assembly 106 which has threads 108 which are configured to engage corresponding threads 110 on the cup 102, thereby forming an enclosed containment vessel for disinfecting contact lenses.

The cap assembly 106 includes a cap 114, as well as a multi-walled, single piece valve body 116 which is affixed to the cap 114. A spring-retaining member 118 is affixed to the valve body 116 and is retained within the cap 114. The cap assembly 106 also includes a stem 120, and the stem 120 is attached to and hermetically sealed to the valve body 116. The stem 120 has a sealing member 122 thereon for sealing with an inside surface 124 of the cup 102. The stem 120 has retaining baskets 126 thereon, and the retaining baskets 126 are configured to pivot open and closed, in order to receive contact lenses, and maintain the contact lenses in a space 128 which is provided between the stem 120 and the retaining baskets 126. The stem 120 and retaining baskets 126 may be conventional, such as described in either U.S. Pat. Nos. 4,200,187 or 4,750,610, both of which are incorporated herein by reference in their entirety.

The spring-retaining member 118 has openings 130 therein for supporting a U-shaped control spring 132. As shown in FIG. 14, preferably the control spring 132 is a beam-like member having a generally U-shaped cross-section, and acts as a beam to transfer an applied pressure induced to control spring supports 134. While FIGS. 9-14 illustrate a specific control spring configuration, the control spring may take other forms.

The headspace 136 of the system 100 includes a lower headspace 136a which is contained generally within the cup 102, and an upper headspace 136b which is contained generally within the cap assembly 106, and there is a communicating passageway 138 which allows gas from the decomposing hydrogen peroxide 104 to travel from the lower headspace 136a, along the communicating passageway 138, to the upper headspace 136b. Approximately 4 to 8 cc's of total overall headspace 136 may be provided, but overall headspace can be varied as can the surface area of the catalyst 140 (i.e., during design), in order to achieve the desired internal operating pressure within the system. This being said, 8 cc's of headspace 136 has been determined to provide a reasonable operating pressure.

A multi-piece catalyst assembly 140 is retained on the end of the stem 120, and an actuating rod 142 also engages the catalyst assembly 140. The actuating rod 142 extends downward through the communicating passageway 138, which assists in its alignment as the actuating rod 142 passes through the stem 120. The system 100 also includes a pressure-displaceable member such as a diaphragm 144 which is held by the spring-retaining member 118. The diaphragm 144 is preferably formed of a suitable elastomeric material and is mounted on and hermetically seals to the valve body 116, where it is held in place by the spring-retaining member 118. A flange 146 on the actuating rod 142 is attached to the diaphragm 144, and is secured in place by a cap 148 on the actuating rod 142. The cap 148 bears against the spring 132, which is suspended in place by control spring supports 134, which are integral parts of the spring-retaining member 118, and pushes the spring 132 into contact with a spring stop 150 which is provided on the inside surface 152 of the cap 114.

The cap assembly 106 also includes a one-way, pressure control valve 154 which consists of a flapper valve 156, and a post 158 which extends through the middle of the flapper valve 156. As will be described more fully later hereinbelow, the pressure control valve 154 is configured to allow venting of the system 100 when the internal pressure reaches a certain point. Vent valves similar to the pressure control valve 154 have been previously employed to control pressure within contact lens cases, for example, and are disclosed in U.S. Pat. No. 4,956,156.

The actuating rod 142 is free to traverse longitudinally within the valve body 116 in response to forces from the diaphragm 144 and control spring 132. The catalyst assembly 140 is sized to complete the reaction within an appropriate time, and is affixed to the actuating rod 142 and the bottom of the stem 120. More specifically, the catalyst assembly 140 may consist of a first catalyst member 160 which is slidable relative to, and generally in and out of, a second catalyst member 162. While the first catalyst member 160 is mounted to the end of the actuating rod 142, the second catalyst member 162 is mounted on the end of the stem 120.

Figure 15:
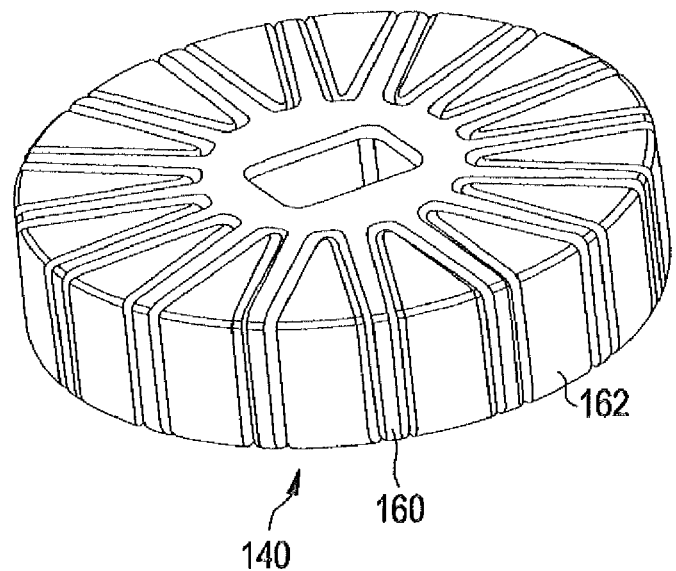
FIG. 15 is a perspective view of a catalyst assembly component of the contact lens disinfecting system shown in FIGS. 10 and 11, showing the catalyst assembly's initial small overall surface area (as provided in FIG. 10)
Figure 16:
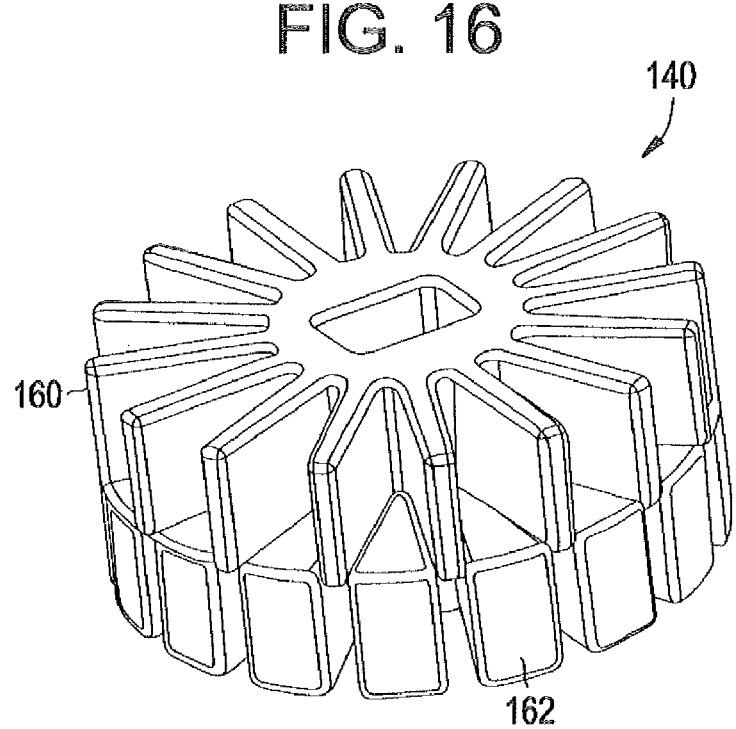
FIG. 16 is a view similar to FIG. 15, but showing the catalyst assembly after deployment, thereby providing an increased overall surface area (as provided in FIG. 11)

While initially the first catalyst member 160 is retained generally within the second catalyst member 162 (see FIG. 10), the actuating rod 142 is shiftable during the disinfecting process, causing the first catalyst member 160 to be pulled generally away from the second catalyst member 162 (see FIG. 11), thereby providing an increased overall surface area of catalyst which is in contact with the hydrogen peroxide. FIG. 15 provides a perspective view of the catalyst assembly 140 showing the catalyst's small surface area as first seen in FIG. 10, while FIG. 16 provides a perspective view of the deployed catalyst after the control spring 132 has been fully deflected by the diaphragm 144 and the actuating rod 142 has deployed the catalyst (as shown in FIG. 11), in response to pressure created by reaction of hydrogen peroxide 104 to its initial, minimally exposed active surface area. In the deployed position as shown in FIGS. 11 and 13, the catalyst assembly 140 preferably offers 1075 sq. mm of effective surface area, almost 10 times the effective area provided by the small effective surface area of the catalyst before deployment (as shown in FIGS. 10 and 15). Depending upon the deflection of the control spring 132, the deployed area of catalyst can be made greater or smaller to as may prove necessary to assure the desired reduction of the hydrogen peroxide to an acceptable level in 6 to 8 hours following introduction of catalyst assembly 140 along with contact lenses to be disinfected.

Preferably, the catalyst assembly 140 provides 67 sq. millimeters of surface area when exposed to the hydrogen peroxide solution 104 when the first catalyst member 160 is retained generally within the second catalyst member 162 as shown in FIGS. 10 and 15, but the first and second catalyst members combined provide 1075 sq. millimeters of surface area once the first catalyst member 160 has been pulled generally out of the second catalyst member 162 as shown in FIGS. 11 and 16. As such, either FIG. 8 or 9 is applicable, depending on at what point in time the actuating rod 142 pivots upward, causing the first catalyst member 160 to pull out of the second catalyst member 162.

Figure 17:
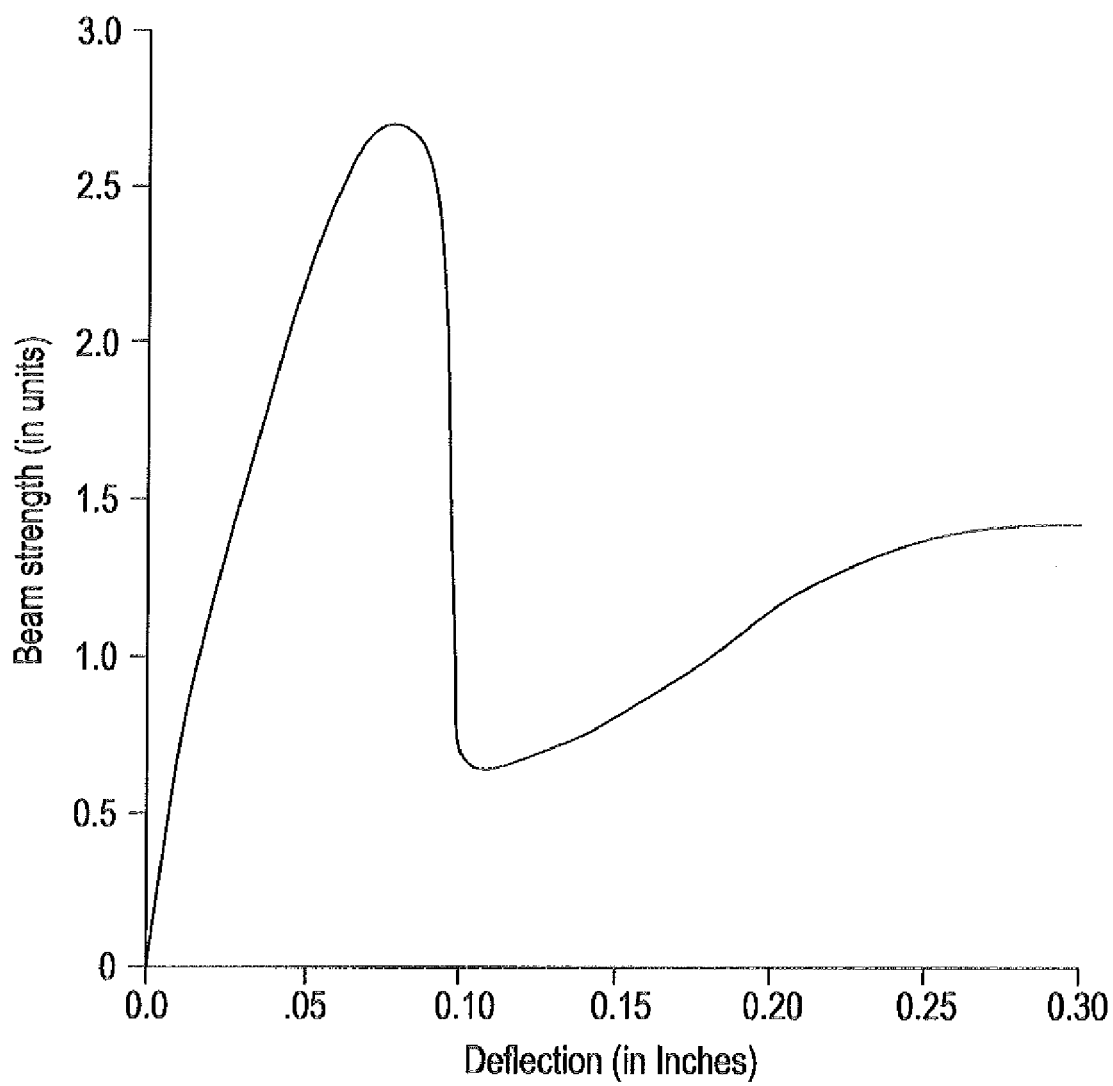
FIG. 17 is a graph which shows how the beam strength of the spring member of FIGS. 10-14 changes based on the amount of deflection.

From a downward starting position as shown in FIG. 10, longitudinal movement of the actuating rod 142 traversing within the valve body 116 is limited by the control spring 132, which is configured to detain the actuating rod's movement until internal pressure resulting from the oxygen released into headspace 136a during disproportionation of hydrogen peroxide 104 after introduction of catalyst assembly 140, enters passage 138, flows past actuating rod 142 to headspace 136b and impinges upon the diaphragm 144. The diaphragm 144, in response to pressure, transfers an upward force to the rod cap 148. The rod cap 148 in turn transfers the load from pressure against diaphragm 144 to control spring 132 which it bears upon. The control spring 132, being "U"-shaped in cross-section, acts as a beam to transfer the pressure-induced load from abutting rod cap 148 to the control spring supports 134 (integral with the spring-retaining member 118), thereby resisting upward movement of the diaphragm 144. As pressure within the headspace 136b against the diaphragm 144 rises (i.e., as a result of the ongoing disproportionation of the hydrogen peroxide 104) to the actuating pressure, approximately 19 p.s.i. in this example, the diaphragm 144 with rod cap 148 gains sufficient force to overcome the control spring 132. In response, the "U"-shape of the control spring 132 begins to deform in a manner in which the cross-sectional height of the "U"-form becomes smaller, causing the beam strength of the control spring 132 to decline. When force delivered by the diaphragm 144 reaches the maximum beam strength of the control spring 132, the control spring 132 flattens and buckles as its cross-section diminishes thereby allowing the diaphragm 144 with rod cap 148, actuating rod 142 and attached first catalyst member 160 to traverse longitudinally upward as shown in FIG. 11, until the control spring 132 abuts the spring stop 150 in the cap 114. The control spring 132 can deflect up to 0.30 inches depending upon the design requirements of the cap assembly 106. In this deformed condition, the control spring 132 offers the diaphragm 144 significantly lower resistance. A typical shape transition in response to bending loads by a spring such as control spring 132 can be more clearly understood by comparing the shape of the control spring 132 in FIG. 10 with its shape shown in FIG. 11, and the spring's resistance forces during such a transition in shape can more clearly be understood by viewing FIG. 17. The control spring 132 shown in FIGS. 10 and 11 demonstrates its maximum beam strength of 2.69 units when the deflection from the force bearing upon it reaches 0.090 inch of travel and its minimum beam strength of 0.64 units, or less than 25% of the maximum, at 0.105 inch of travel just 0.025 of an inch later. When fully deflected as described above, the control spring 132 offers approximately 1.42 pounds of resistance (44% of the original deflection force) to the force from diaphragm 144, and remains solidly pressed against the spring stop 150 while under as little as 12 p.s.i. of pressure in the headspace 136.

Gas entering the headspace 136b and contained by the diaphragm 144 can only escape to the ambiance by means of the pressure control valve 154. The flapper valve 156, retained on the post 158, communicates with the headspace 136 through a port 164. Venting of the headspace 136 is precipitated as oxygen gas, under pressure against flapper valve 156, is allowed to vent at an annular junction between the flapper valve 156 and the post 158, exit through passage 166, and slowly escape to the ambiance along the close fitting, but unsealed interface between the valve body 116 and the top 112 of the cup 102 and between the threads 108 on the valve body 116 and threads 110 on the cup 102, once a threshold pressure of 24 p.s.i. to 36 p.s.i., for example, has been reached. Such venting ceases as the flapper valve 156 reseals against the post 158 after pressure against it has decreased to a level below that of the original threshold pressure, which for this example would be approximately 3 p.s.i. to 8 p.s.i. lower than the threshold pressure. In the system 100 shown in FIGS. 10 and 11, a resealing pressure as low as 12 p.s.i. bearing against the diaphragm 144 would exert over 1.42 pounds of force against the control spring 132. This force would be adequate to hold the control spring 132 solidly against the spring stop 150, as can be seen in FIG. 11, wherein the control spring 132 requires only 0.66 pounds of force to maintain its deflection of 0.11 inches and 0.81 pounds of force to maintain its deflection of 0.15 inches and 1.42 pounds to maintain a deflection of 0.30 inches. Pressure within the headspace 136, after initial venting, fluctuates between the pressure control valve's vent pressure and its resealing pressure but would not normally drop below its resealing pressure as decomposition of hydrogen peroxide proceeds to completion under the influence of the catalyst, whose greater effective surface area now exposed, dramatically increases the rate of disproportionation (see FIG. 8) over its initially low effective surface area prior to being deployed.

Preferably, sufficient threads 108, 110 are provided for engaging the cup 102 with the cap assembly 106 to allow the seal 122 to pass a chamfer 168 at the top 112 of the cup 102, in order to relieve the low residual pressure maintained by the pressure control valve 854, prior to final unthreading of the cap assembly 106 from the cup 102. Conversely, during installation of the cap assembly 106, sufficient engagement is provided before the seal 122 passes below the chamfer 168 in order to assure that adequate structure is engaged for containment of pressure generated during disinfection.

Concurrent with deployment of the large catalyst, the rate of catalytically-inspired disproportionation of hydrogen peroxide solution 104 within the cup 102 increases significantly in response to the overall surface area of catalyst becoming enlarged. Solution temperature rises with the increased disproportionation giving rise to thermally-inspired convection currents, and mixing currents are also generated by the deployment motion of the catalyst assembly and as oxygen bubbles form along it and rise through the solution. These resulting currents initially speed the catalytic decomposition by disturbing stratification to bring more peroxide molecules into contact with the catalyst assembly 140. Oxygen continues to be evolved into the headspace 136 and its pressure is controlled by the cyclic venting of the control valve 154, previously described, as final decomposition of the solution lowers peroxide concentration toward an ocularly safe level for use of the contact lenses disinfected within.

Figure 12:
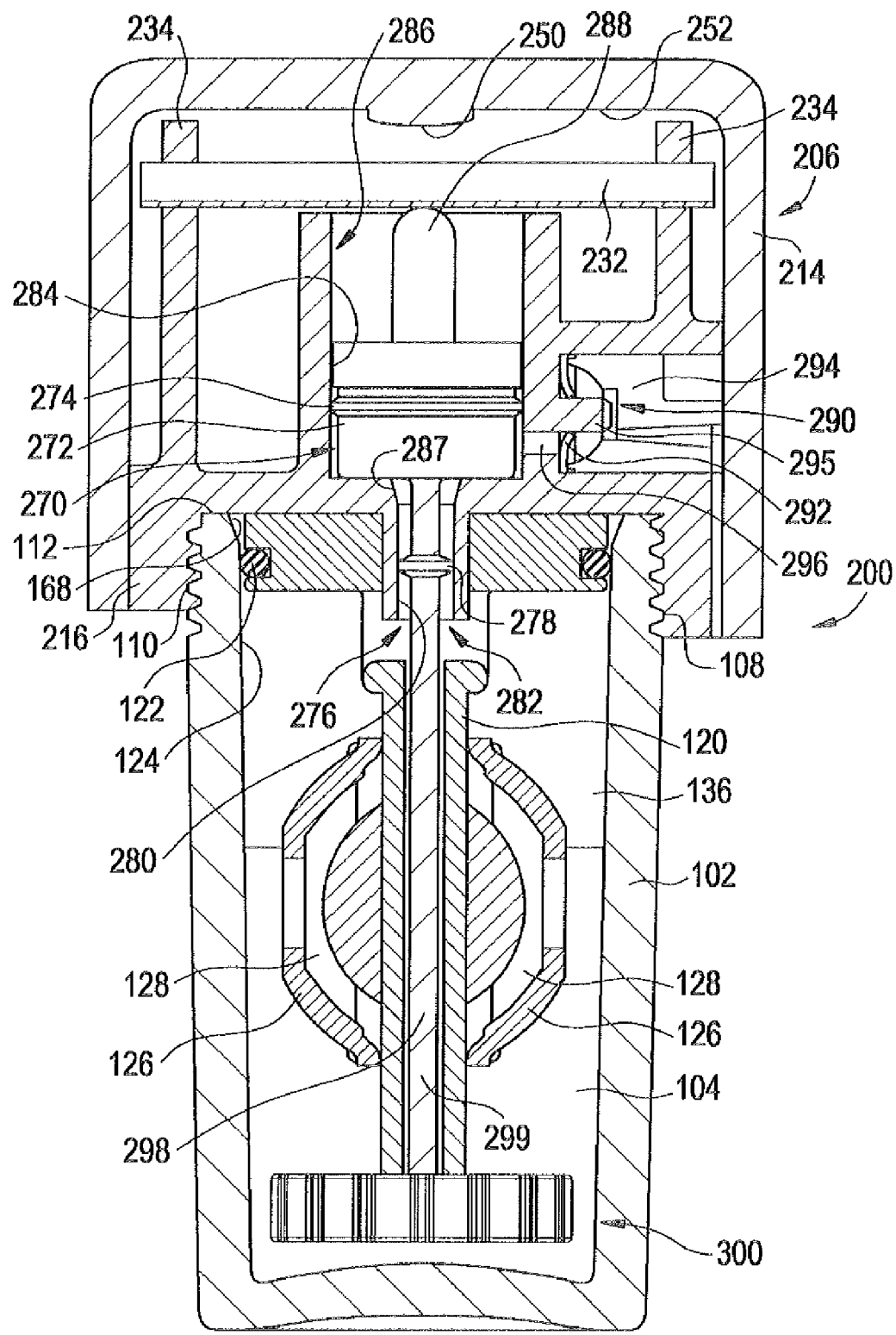
FIGS. 12 and 13 are cross-sectional views of a contact lens disinfecting system which is in accordance with another embodiment of the present invention.
Figure 13:
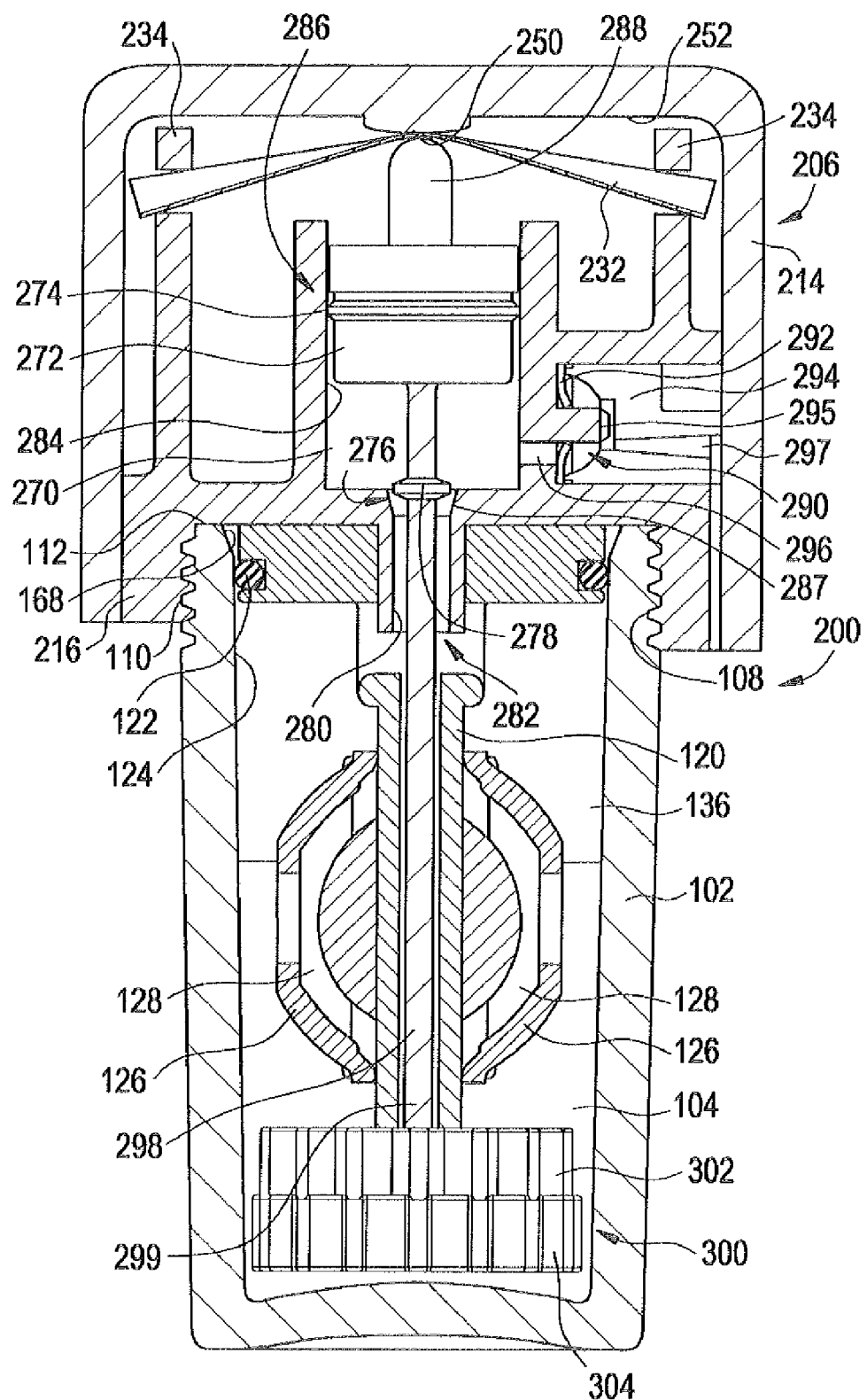
Figure 14:
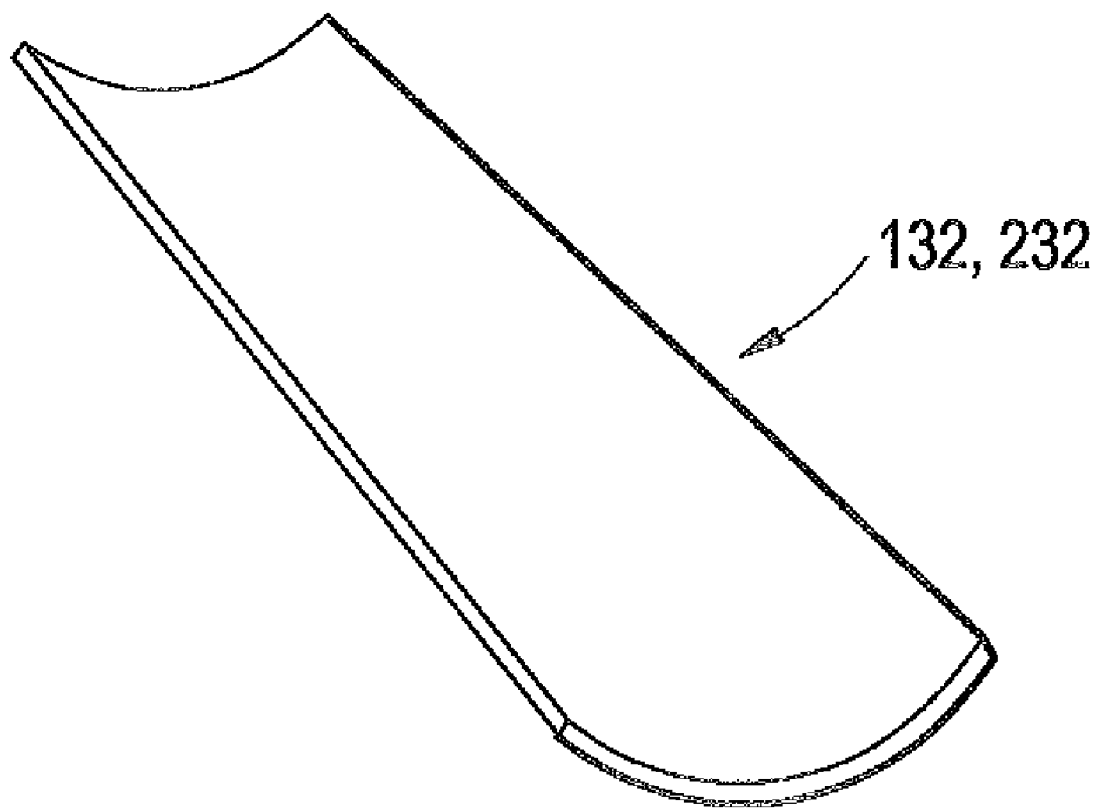
FIG. 14 is a perspective view of a spring member component of the contact lens disinfecting systems shown in FIGS. 10 through 13.

An alternate embodiment to the contact lens disinfection system 100 shown in FIGS. 10 and 11 is shown in FIGS. 12 and 13. This system 200, operating as discussed below, is capable of achieving elevated pressures sufficient to exploit additive effect during disinfection. Since the available variations are almost limitless, it should be understood that although the designs discussed herein have been provided to illustrate operation, it is not intended to limit the variety of design iterations possible within the overall concept.

Like the contact lens disinfection system 100 previously described, the contact lens disinfection system 200 shown in FIGS. 12 and 13 includes a cup 102 and a cap assembly 206. The cap assembly 206 has a sealing member 122 thereon which engages and seals with an inside surface 124 of the cup 102. The cup 102 is configured to retain hydrogen peroxide solution 104 therein, with headspace 136 being provided above the hydrogen peroxide solution 104. For example, the system 200 may be configured such that when 10 milliliters of hydrogen peroxide 104 is contained in the cup 102, and the cap assembly 206 is engaged with the top 112 of the cup 102, there is 4 cc's of headspace 136 provided above the hydrogen peroxide 104. However, the volume of headspace 136 can certainly be varied, as can the volume of hydrogen peroxide solution 104 used for the disinfection process.

The cap assembly 206 includes a cap 214, a valve body 216 which is attached to the cap 214, and a stem 120 which is attached and hermetically sealed to the valve body 216. The stem 120 has pivotable retaining baskets 126 thereon for retaining the contact lenses in a space 128 between the stem 120 and the baskets 126.

The cap assembly 206 also includes a U-Shaped control spring 232 which is retained by the valve body 216. Specifically, the control spring 232 is suspended in place by control spring supports 234, which are integral parts of the valve body 216. The control spring 232 of system 200 is preferably exactly the same as the control spring 132 employed in system 100.

The system 200 also includes a plunger 270. The plunger 270 includes a cylindrical portion 272 which has a plunger seal 274 thereon, as well as a piston 276 which provides a piston seal 278. Preferably, both seals 274, 278 are formed of a suitable elastomeric material. While the piston seal 278 engages an inside wall 280 of a piston cylinder area 282 of the valve body 216, the plunger seal 274 engages an inside wall 284 of a plunger cylinder area 286 of the valve body 216. An upper tip 288 of the plunger 270 is provided as being a domed surface, and the plunger tip 288 engages the control spring 232. The plunger 270 is configured to traverse up and down, causing the plunger seal 274 to slide along the inside wall 284 of the plunger cylinder area 286, and causing the piston seal 278 to slide along, and into and out of engagement with, the inside wall 280 of the piston cylinder area 282. When the plunger 270 traverses upward, the plunger tip 288 pushes the control spring 232 into contact with a spring stop 250 which is provided on the inside surface 252 of the cap 214.

The cap assembly 206 also includes a one-way pressure control valve 290 which consists of a flapper valve 292 which is retained by a retainer 294, and a post 295 which extends through the middle of the flapper valve 292. There is a vent port 296 on one side of the flapper valve 292 and a vent passage 297 on the other side of the flapper valve 292. As will become more apparent hereinbelow, the piston seal 278 acts as a first valve in the system while the one-way pressure control valve 290 acts as a second valve in the system 200, further downstream in the venting process. Specifically, the plunger 270 gets pushed upward once pressure in the system reaches a sufficiently high level, causing the piston seal 278 to slide out of engagement with the inside wall 280 of the piston cylinder area 282. As such, the first valve opens. Thereafter, the system 200 vents through the second valve, i.e., one-way pressure control valve 290.

A bottom portion 298 of the plunger 270 provides an actuating rod 299 which extends through the stem 120 and engages a catalyst assembly 300. A bottom of the stem 120 also engages the catalyst assembly 300. More specifically, the catalyst assembly 300 consists of a first catalyst member 302 which is slidable relative to, and generally in and out of a second catalyst member 304. While the first catalyst member 302 is mounted to the end of the actuating rod 299, the second catalyst member 304 is mounted on the end of the stem 120.

While initially the first catalyst member 302 is retained generally within the second catalyst member 304 (see FIG. 12), the plunger 270 (and integral actuating rod 299) is shiftable causing the first catalyst member 302 to be pulled generally away from the second catalyst member 304 (see FIG. 13), thereby providing an increased overall surface area of catalyst which is in contact with the hydrogen peroxide. In the deployed position as shown in FIG. 13, the catalyst assembly preferably offers 1075 sq. mm of effective surface area. Depending upon the deflection of the control spring 232 of system 200, the deployed area of catalyst can be made greater or smaller as may prove necessary to assure the desired reduction of the hydrogen peroxide to an acceptable level in 6 to 8 hours following introduction of catalyst assembly along with contact lenses to be disinfected.

Preferably, the catalyst assembly 300 provides 65 to 110 sq. mm of surface area when exposed to the hydrogen peroxide solution when the first catalyst member 302 is retained generally within the second catalyst member 304 as shown in FIG. 12, but the first and second catalyst members combined provide 1075 sq. mm of surface area once the first catalyst member 302 has been pulled generally out of the second catalyst member 304 as shown in FIG. 13.

The catalyst assembly 300, sized to complete the reaction within an appropriate time, is affixed to the actuating rod 299 and to the bottom of the stem 120 to assure that the catalytically-stimulated disproportionation reaction only begins when contact lenses contained in the space 128 between the stem 120 and the baskets 126 are immersed simultaneously with introduction of the catalyst assembly 300 into the hydrogen peroxide disinfection solution 104. As discussed, approximately 4 cc's of headspace 136 for containment of evolved oxygen gas is preferably provided; however, this volume can be varied as can the volume of solution 104, the ratio between these two items and the overall surface area of the catalyst in order to alter disinfection times and pressures, as previously discussed. Disinfection solution and pressure is contained between the cup 102 and the cap assembly 206 by the seals 122, 278, as shown in FIG. 12. The entire subassembly of the plunger 270 is free to traverse within the plunger cylinder area 286 with its attached piston 276 and actuating rod 299 traversing within the piston cylinder area 282 of the valve body 216.

From a starting position as shown in FIG. 12, the catalyst assembly 300 preferably provides only 65 sq. mm to 110 sq. mm of active catalyst surface area to initiate disproportionation of hydrogen peroxide and thereby create pressure in headspace 136 from the expanding evolved oxygen. After simultaneous immersion of the catalyst assembly 300 with the end of stem 120 into the hydrogen peroxide solution 104, along with the contact lenses to be disinfected being contained within the spaces 128, pressure developing within the headspace 136 impinges upon the piston seal 278 and tends to push the plunger 270 up. This causes the plunger tip 288 to bear upon the control spring 232. The control spring 232 acts as a beam to transfer the pressure-induced load to the control spring supports 234, thereby resisting upward movement of plunger 270. As pressure within the headspace 136 continues to increase from the ongoing disproportionation, and the plunger 270 traverses upward in response, the "U"-shape of the control spring 232 deforms in a manner in which the cross-sectional height of the "U"-form becomes smaller and the beam strength of the control spring 232 declines. When the combination of the force delivered by the plunger tip 288 reaches the maximum beam strength of the control spring 232, the spring 232 flattens and buckles allowing the plunger 270 to move upward until the control spring 232 contacts the spring stop 250 on the inside surface 252 of the cap 214, as shown in FIG. 13. In this deformed condition, the control spring 232 offers the plunger 270 significantly lower resistance. Typical resistance to a bending force offered by a spring such as the control spring 232 has been previously discussed hereinabove and can more clearly be understood by viewing FIG. 17. As the piston 276 continues to traverse upward in response to pressure within the headspace 136, the plunger tip 288 begins to deform the control spring 232, and the piston seal 278 exits the piston cylinder area 282 and enters a transition section 287 which serves to connect the piston cylinder area 282 and the plunger cylinder area 286. Once the piston seal 278 has exited the piston cylinder area 282, pressure within the headspace 136 is free to flow through the transition section 287 and into the plunger cylinder area 286 and hear upon the cylindrical portion 272 of the plunger 270, thereby driving the plunger 270 with increased force, along with plunger tip 288 upward against the control spring 232, whereupon contact with the spring stop 250 limits its deformation.

Figure 5:
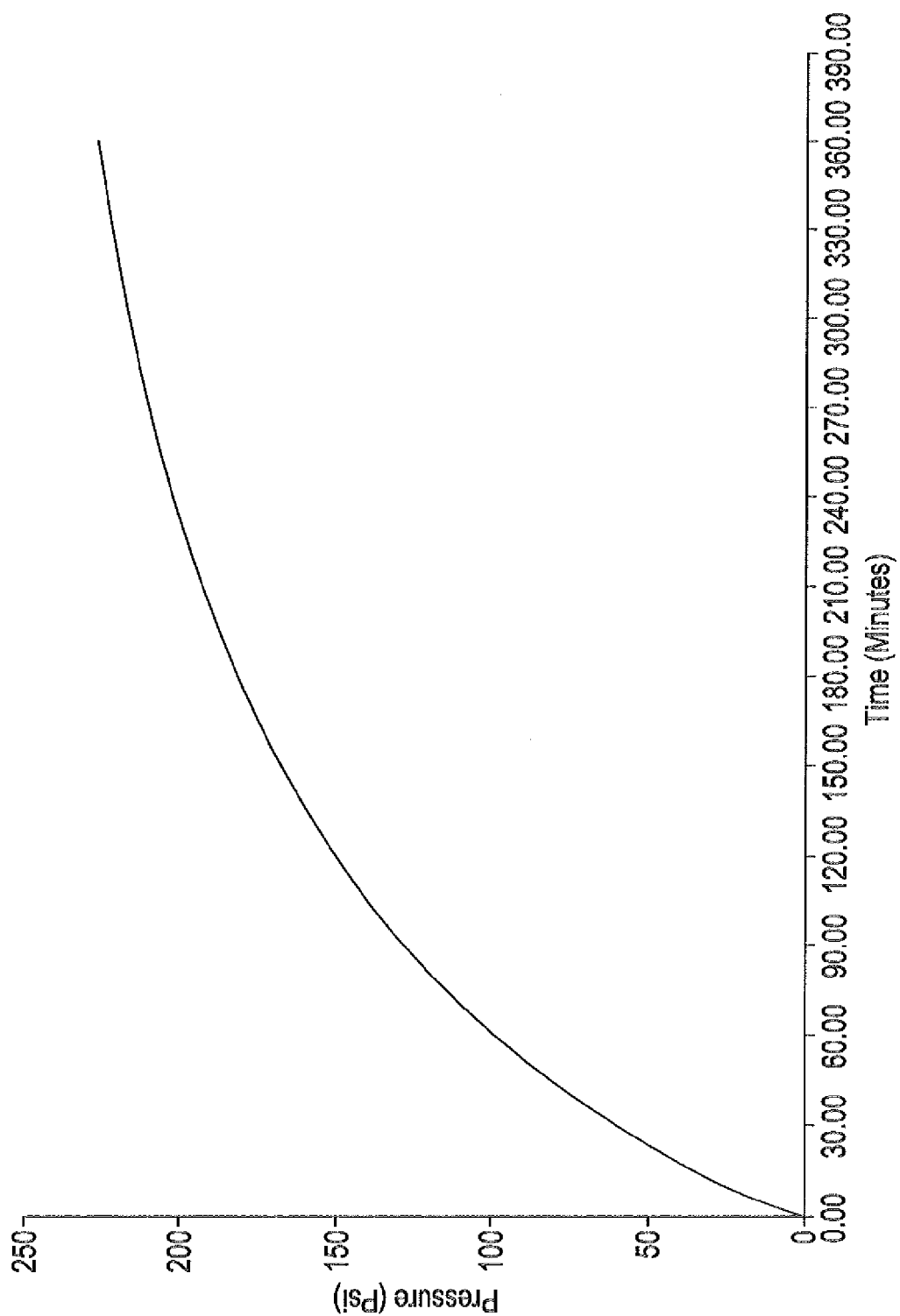
FIG. 5 is a graph which shows the change in pressure over time when a 110 sq. mm catalyst is immersed in 10 milliliters of 3.7% hydrogen peroxide solution in a container having 6 cc's of headspace.

As shown in FIG. 5, with 10 milliliters of 3.7% peroxide in the cup 102, pressure within a headspace of 4 cc's would, for example, reach 100 p.s.i. in approximately 60 minutes and concentration of the solution would remain above 2.7% (see FIG. 6) if the catalyst assembly had an initial active surface area of 110 sq. mm. This process significantly delays any substantial catalytic reduction of the peroxide concentration during that period of time compared to the typical decomposition rate (see FIG. 3), thereby increasing the overall effectiveness of the system to kill undesirable pathogenic organisms as illustrated in FIG. 4. If, for example, the piston seal 278 were 0.185 inches in diameter, the plunger tip 288 would exert a bending force against the control spring 232 of 2.7 pounds once 100 p.s.i. of pressure was reached within the headspace 136 in system 200. By comparison, plunger 270, if 0.50 inches in diameter, would have the potential to exert 19.6 pounds of force against the control spring 232 when exposed to 100 p.s.i. of pressure.

This force would be, at most, only momentary however due to provision of the one way, pressure sensitive, low pressure, pressure control valve 290 which is in communication with the pressurized gas flowing into the space enclosed by the plunger cylinder area 286. Gas entering the plunger cylinder area 286 is contained by the plunger seal 274 and can only escape to the ambiance by means of the pressure control valve 290. The flapper valve 292, retained on post 295 by retainer 294, communicates with the interior of the plunger cylinder area 286 through port 296 and with the ambiance through passage 297. Decompression of the headspace 136 in system 200 continues as oxygen gas under pressure against the flapper valve 292 is allowed to vent at the annular junction between the flapper valve 292 and the post 295 and exits to the ambiance through passage after a threshold pressure of 24 p.s.i. to 36 p.s.i., for example, has been reached. Such venting ceases as the flapper valve 292 reseals against the post 295 after internal pressure has declined to a level below that of the original threshold pressure which for this example would be approximately 3 p.s.i. to 8 p.s.i. lower than the threshold pressure. In the immediate example, with a resealing pressure of 12 p.s.i., the plunger 270 would exert 2.36 pounds of force against the control spring 232, holding it solidly against the spring stop 250 as can be seen by viewing the spring force curve shown in FIG. 17, wherein the control spring 232 requires only 0.66 pounds of force to maintain its deflection of 0.11 inches of travel, 0.81 pounds of force to maintain its deflection of 0.15 inches and 1.42 pounds of force to maintain its deflection of 0.30 inches. At 12 p.s.i., the force exerted by plunger 270 would be sufficient to keep the control spring 232 fully deflected and thus maintain communication between the headspace 136 and the flapper valve 292.

Deflection of the control spring 232 allows the plunger 270 to rise to its maximum extension to withdraw the first catalyst member 302 from the second catalyst member 304, thereby increasing the available overall active catalyst surface area from the initial minimum of 65 to 110 sq. mm, to 1075 sq. mm. Movement of the catalyst creates mixing currents as will the expanding and rising bubbles from oxygen boiling from the solution and thermal currents resulting from heat generated by the catalytically-inspired disproportionation, and these resulting currents initially speed the catalytic decomposition by disturbing stratification to bring more peroxide molecules into contact with the catalyst. By this process the peroxide will have been maintained at a high concentration for an extended period of time for improved efficacy in killing pathogenic organisms as compared to present day competitive systems. Further, although delayed from introduction, the significantly larger active surface area of the deployed catalyst assures that peroxide concentration is reduced more rapidly to a desirable safe level at the end of a 6 to 8 hour period.

Figure 18:
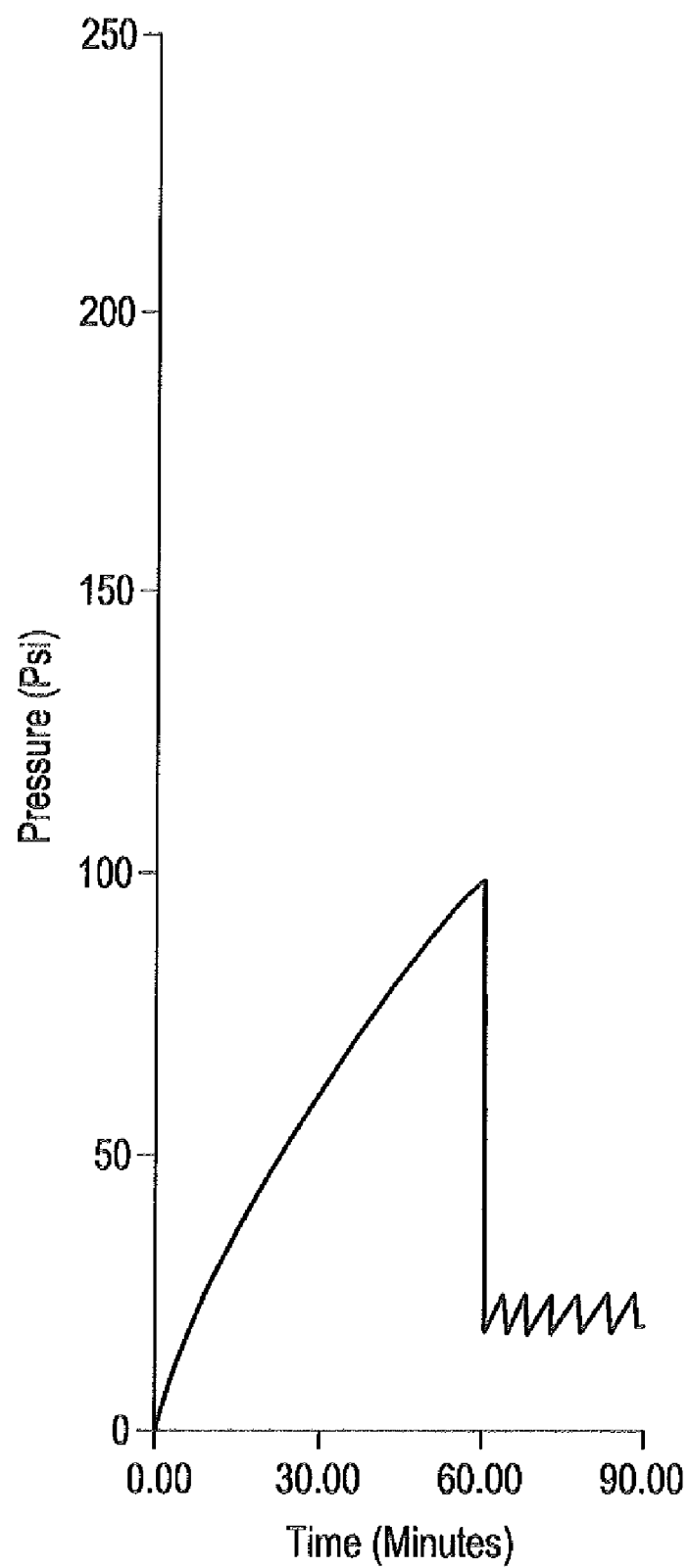
FIG. 18 is a graph which shows the change in pressure over time when the contact lens disinfection system shown in FIGS. 12 and 13 is employed.

As disclosed above, pressure within the headspace 136 in system 200 initially rises to the high pressure level established by the control spring 232 resisting force from the plunger 270, and then drops precipitously during venting when the piston 276 enters the transition area 287, after which the pressure rises and falls slightly as it responds to low pressure control provided by the pressure control valve 290 as shown in FIG. 18. After initial venting, pressure within the headspace 136 in system 200 fluctuates between the vent pressure and the resealing pressure of the pressure control valve 290, but does not normally drop below its resealing pressure. This low level rising and falling pressure pattern continues for several hours after venting as decomposition of hydrogen peroxide continues to lower peroxide concentration down to an ocularly safe level.

Just like with system 100, preferably system 200 provides that there are sufficient threads 108, 110 for engaging the cup 102 with the cap assembly 206 to allow the seal 122 to pass a chamfer 168 at the top 112 of the cup 102, in order to relieve the low residual pressure maintained by the pressure control valve 290, prior to final unthreading of the cap assembly 206 from the cup 102. Conversely, during installation of the cap assembly 206, sufficient engagement is provided before the seal 122 passes below the chamfer 168 in order to assure that adequate structure is engaged for containment of pressure generated during disinfection.

In addition to sustaining a high concentration of hydrogen peroxide for an extended period of time, decompression resulting from the release of high pressure within the system 200 described herein provides an additive effect to the disinfection process when oxygen occupying headspace 136 is vented through the controlled movement of piston 276, allowing saturated oxygen within the hydrogen peroxide disinfection solution 104 to boil off as pressure in the headspace 136 drops to a controlled low level much more quickly than a pathogenic organism could adjust in order to maintain its dynamic equilibrium.

It should be pointed out that the terms "catalyst" and "catalyst assembly" are used somewhat interchangeably above in connection with describing the embodiments of the invention. It is preferred that a multi-component catalyst assembly be employed consisting of a plurality of catalyst members which are moveable relative to each other to provide for a changing surface area which is exposed to the solution. One or more of the catalyst members (or one or more portions thereof) may be coated with, for example, platinum to provide for an enhanced catalytic effect with regard to the solution. While the above description refers to a first catalyst member being moved relative to second catalyst member, it should be understood that the contact lens cases disclosed herein could be configured such that the second catalyst member is moveable relative to the first catalyst member. Alternatively, the contact lens cases could be configured to operate with a multi-piece catalyst assembly having more than two pieces.

While specific embodiments of the present invention have been shown and described, it is envisioned that those skilled in the art may devise various modifications of the present invention without departing from the spirit and scope of the present invention.

What is claimed is:

1. A disinfecting system for using solution to disinfect an object, said disinfecting system comprising: a cup configured to retain the solution therein; a catalyst assembly, wherein the system is configured to move at least one piece of the catalyst assembly relative to at least one other piece of the catalyst assembly in response to pressure in the system, thereby providing that the effective surface area of the catalyst assembly which is exposed to the solution increases during disinfection of the object within the cup, wherein the catalyst assembly comprises a first catalyst member and a second catalyst member, further comprising an actuating rod which engages at least one of the first catalyst member and the second catalyst member, a stem which engages at least one of the first catalyst member and the second catalyst member, and wherein the actuating rod is moveable relative to the stem, thereby providing that one of the first catalyst member and second catalyst member is moveable relative to the other of the first catalyst member and second catalyst member.

2. A disinfecting system as recited in claim 1, further comprising a cap assembly, said cap assembly comprising a cap, a valve body in contact with the cap, a control spring, and a spring-retaining member which retains the control spring and which is engaged with the valve body and is disposed within the cap.

3. A disinfecting system as recited in claim 2, wherein the cap assembly comprises a one-way pressure control valve which is configured to allow venting of the system while preventing foreign matter from entering the system.

4. A disinfecting system as recited in claim 2, wherein the system comprises a lower headspace which is contained within the cup, an upper headspace which is contained within the cap assembly, and a communicating passageway which is configured to allows gas from decomposing solution to travel from the lower headspace, along the communicating passageway, to the upper headspace.

5. A disinfecting system as recited in claim 4, wherein the actuating rod extends downward through the communicating passageway.

6. A disinfecting system as recited in claim 5, further comprising a pressure-displaceable member which is retained by the spring-retaining member.

7. A disinfecting system as recited in claim 6, wherein the actuating rod is engaged with the pressure-displaceable member, and the pressure-displaceable member is secured in place by a cap on the actuating rod, wherein the cap on the actuating rod bears against the control spring.

8. A disinfecting system as recited in claim 7, wherein the cap assembly further comprises a one-way pressure control valve which is configured to allow venting of the system while preventing foreign matter from entering the system.

9. A disinfecting system as recited in claim 7, wherein the actuating rod is configured to traverse longitudinally within the valve body in response to forces from the pressure-displaceable member and control spring.

10. A disinfecting system as recited in claim 9, wherein longitudinal movement of the actuating rod traversing within the valve body is limited by the control spring, wherein the control spring is configured to detain movement of the actuating rod until internal pressure resulting from gas released into the lower headspace, enters communicating passageway, flows to upper headspace, and impinges upon the pressure-displaceable member, wherein the pressure-displaceable member, in response to pressure, is configured to transfer a force to the cap of the actuating rod, wherein the cap of the actuating rod transfers force to the control spring, wherein the control spring is configured to resist upward movement of the pressure-displaceable member, wherein as pressure within the upper headspace against the pressure-displaceable member rises, the pressure-displaceable member gains sufficient force to overcome the control spring, whereafter the actuating rod traverses longitudinally relative to the stem, causing the effective surface area of the catalyst exposed to the solution to increase.

11. A disinfecting system as recited in claim 2, further comprising a plunger having a first seal thereon which contacts and seals against an internal wall of the valve body, wherein the plunger comprises a portion which extends from the cylindrical portion, wherein the portion which extends from the cylindrical portion of the plunger has a second seal thereon which also contacts and seals against an internal wall of the valve body, wherein the second seal comprises a first valve of the system, and wherein the system further comprises a one-way pressure control valve, said one-way pressure control valve comprising a second valve of the system, wherein the system is configured such that upon sufficient pressure resulting in the system, the plunger moves thereby causing the second seal to move out of contact with the internal wall of the valve body, thereby opening said first valve, whereafter the system vents through the second valve via gas in the system venting through the one-way pressure control valve.

12. A disinfecting system as recited in claim 1, further comprising a cap assembly which comprises a cap, a valve body, a control spring, a spring-retaining member which retains the control spring, is engaged with the valve body, and is disposed within the cap, a plunger having a seal thereon which contacts and seals against the valve body, wherein the plunger comprises a portion which extends from the cylindrical portion and provides the actuating rod, wherein the portion which extends from the cylindrical portion of the plunger also has a seal thereon which contacts and seals against the valve body, wherein the plunger is configured to traverse up and down, causing the seal on the cylindrical portion of the plunger to slide along a surface of the valve body, and causing the seal on the portion which extends from the cylindrical portion of the plunger to slide along, and into and out of engagement with, a surface of the valve body.

13. A disinfecting system as recited in claim 12, wherein a vent port is provided in the valve body, between the seal on the cylindrical portion of the plunger and the seal on the portion which extends from the cylindrical portion of the plunger.

14. A disinfecting system as recited in claim 13, further comprising a vent passage and a valve between the vent port and the vent passage.

15. A disinfecting system for using solution to disinfect an object, said disinfecting system comprising: a catalyst assembly; an actuating rod which engages at least one piece of the catalyst assembly; a stem which is configured to retain the object as well as at least one other piece of the catalyst assembly; a one-way pressure control valve; and a mechanism which is configured to respond to pressure within the system and effect movement of the actuating rod, thereby causing the at least one piece of the catalyst assembly to move relative to at least one other piece of the catalyst assembly, wherein the disinfecting system is configured such that movement of the actuating rod causes an increase in the effective surface area of the catalyst assembly which is exposed to the solution, wherein the system is configured such that venting of the system occurs through the one-way pressure control valve upon the mechanism responding to pressure within the system and effecting movement of the actuating rod.

16. A disinfecting system as recited in claim 15, further comprising a cap assembly, said cap assembly comprising a cap, a valve body in contact with the cap, a control spring, and a spring-retaining member which retains the control spring and which is engaged with the valve body and is disposed within the cap.

17. A disinfecting system as recited in claim 16, wherein the stem is engaged with the valve body and has a sealing member thereon for sealing with an inside surface of the cup.

18. A disinfecting system as recited in claim 17, wherein the system comprises a lower headspace which is contained within the cup, an upper headspace which is contained within the cap assembly, and a communicating passageway which is configured to allows gas from decomposing solution to travel from the lower headspace, along the communicating passageway, to the upper headspace.

19. A disinfecting system as recited in claim 15, further comprising a cap assembly, wherein the system comprises a lower headspace which is contained within the cup, an upper headspace which is contained within the cap assembly, and a communicating passageway which is configured to allow gas from decomposing solution to travel from the lower headspace, along the communicating passageway, to the upper headspace, wherein the actuating rod extends downward through the communicating passageway.

20. A disinfecting system as recited in claim 19, wherein the cap assembly comprises a cap, a valve body in contact with the cap, a control spring, a spring-retaining member which retains the control spring and which is engaged with the valve body and is disposed within the cap, and a pressure-displaceable member which is retained by the spring-retaining member.

21. A disinfecting system as recited in claim 20, wherein the actuating rod is engaged with the pressure-displaceable member, and the pressure-displaceable member is secured in place by a cap on the actuating rod, wherein the cap on the actuating rod bears against the control spring.

22. A disinfecting system as recited in claim 21, wherein the actuating rod is configured to traverse longitudinally within the valve body in response to forces from the pressure-displaceable member and control spring.

23. A disinfecting system as recited in claim 22, wherein longitudinal movement of the actuating rod traversing within the valve body is limited by the control spring, wherein the control spring is configured to detain movement of the actuating rod until internal pressure resulting from gas released into the lower headspace, enters communicating passageway, flows to upper headspace, and impinges upon the pressure-displaceable member, wherein the pressure-displaceable member, in response to pressure, is configured to transfer a force to the cap of the actuating rod, wherein the cap of the actuating rod transfers force to the control spring, wherein the control spring is configured to resist upward movement of the pressure-displaceable member, wherein as pressure within the upper headspace against the pressure-displaceable member rises, the pressure-displaceable member gains sufficient force to overcome the control spring, whereafter the actuating rod traverses longitudinally relative to the stem, causing the effective surface area of the catalyst exposed to the solution to increase.

24. A disinfecting system as recited in claim 16, further comprising a plunger having a first seal thereon which contacts and seals against an internal wall of the valve body, wherein the plunger comprises a portion which extends from the cylindrical portion, wherein the portion which extends from the cylindrical portion of the plunger has a second seal thereon which also contacts and seals against an internal wall of the valve body, wherein the second seal comprises a first valve of the system, wherein the one-way pressure control valve comprises a second valve of the system, wherein the system is configured such that upon sufficient pressure resulting in the system, the plunger moves thereby causing the second seal to move out of contact with the internal wall of the valve body, thereby opening said first valve, whereafter the system vents through the second valve via gas in the system venting through the one-way pressure control valve.

25. A disinfecting system as recited in claim 24, wherein a vent port is provided in the valve body, between the seal on the cylindrical portion of the plunger and the seal on the portion which extends from the cylindrical portion of the plunger.

26. A disinfecting system as recited in claim 25, further comprising a vent passage and a valve between the vent port and the vent passage.

* * * * *